(12) United States Patent
Gittelson

(10) Patent No.: US 7,429,175 B2
(45) Date of Patent: Sep. 30, 2008

(54) DENTAL IMPLANT SURGICAL GUIDE

(76) Inventor: Glenn L. Gittelson, 3130 Denton Dr., Merrick, NY (US) 11566

( * ) Notice: Subject to any disclaimer, the term of this patent is extended or adjusted under 35 U.S.C. 154(b) by 0 days.

(21) Appl. No.: 11/594,400

(22) Filed: Nov. 8, 2006

(65) Prior Publication Data

US 2007/0111156 A1    May 17, 2007

Related U.S. Application Data

(60) Provisional application No. 60/737,789, filed on Nov. 17, 2005.

(51) Int. Cl.
*A61C 3/00* (2006.01)
*A61C 19/04* (2006.01)
*A61C 8/00* (2006.01)

(52) U.S. Cl. ............... 433/75; 433/72; 433/173

(58) Field of Classification Search .................... 433/72, 433/75, 172–173
See application file for complete search history.

(56) References Cited

U.S. PATENT DOCUMENTS

| | | | |
|---|---|---|---|
| 4,543,065 A * | 9/1985 | Bushway | ...................... 433/221 |
| 5,133,660 A | 7/1992 | Fenick | |
| 5,556,278 A | 9/1996 | Meitner | |
| 5,636,986 A | 6/1997 | Pezeshkian | |
| 5,813,858 A | 9/1998 | Singer | |
| 5,931,675 A | 8/1999 | Callan | |
| 6,024,567 A | 2/2000 | Callan | |
| 6,164,969 A | 12/2000 | Dinkelacker | |
| 6,290,500 B1 | 9/2001 | Morgan et al. | |
| 6,431,867 B1 | 8/2002 | Gittelson et al. | |
| 6,558,162 B1 | 5/2003 | Porter et al. | |
| 6,793,491 B2 | 9/2004 | Klein et al. | |
| 7,086,860 B2 | 8/2006 | Schuman et al. | |
| 2003/0170591 A1 | 9/2003 | Kurer | |
| 2004/0048225 A1 | 3/2004 | Fletcher | |
| 2007/0065771 A1 * | 3/2007 | Kohani | ........................ 433/74 |

* cited by examiner

*Primary Examiner*—John J Wilson
*Assistant Examiner*—Heidi M Bashaw
(74) *Attorney, Agent, or Firm*—Roberts Mardula & Wertheim, LLC

(57) ABSTRACT

A prefabricated dental implant surgical guide. The implant surgical guide comprises a tooth shaped contour which simulates a natural tooth and the final prosthesis. The tooth shaped contours can be shaped to match any tooth found in the mouth. The system further comprises apical posts which protrude from the apical aspect of the tooth contour of the surgical guide. These apical posts are capable of marking an initial osteotomy site. The apical posts are further able to be placed in to an initial and developing osteotomy site to verify proper implant location, angulation and rotational position prior to implant placement. Significantly the apical post can be attached to the surgical guide and of a fixed length. The apical post can also be adjustable allowing continuous osteotomy site verification and removable allowing an implant surgical drill to pass thru it thereby allowing continuous osteotomy site development and verification. The system further comprises a coronal post aspect to position the surgical guide. The posts can be removed, the tooth contour aspect of the guide hollowed out and then relined and secured to the abutment aspect of an implant thereby functioning as a provisional crown or crowns. The prefabricated dental implant surgical guide can be used to place single implants or multiple side by side implants in a continuous fashion allowing verification of implant location, angulation and rotational position prior to implant placement leading to a more esthetic, functional and stable prosthesis.

12 Claims, 19 Drawing Sheets

DENTAL IMPLANT SURGICAL GUIDE

CROSS REFERENCE TO RELATED APPLICATIONS

This application claims priority under 35 U.S.C. §119(e) from provisional application No. 60/737,789 filed Nov. 17, 2005. The Ser. No. 60/737,789 application is incorporated by reference herein, in its entirety, for all purposes.

BACKGROUND

This application relates generally to oral implant surgery. More particularly the present invention relates to a surgical guide to be used during dental implant surgery which is used to effect correct placement of a dental implant.

In the healthy non-diseased mouth with natural teeth present, there exists a biologic relationship between the root of a tooth, the crown of a tooth, the bone surrounding the root and the gingiva (soft tissue) surrounding the bone, root and crown of a tooth. In nature, the shape and contour that the gingiva or soft tissue assumes and follows is dictated by the underlying presence and shape of bone. The bone contours around a natural tooth are actually scalloped, with the bone more apical on the facial and lingual aspects of the tooth and more coronal in the inter-proximal area (between the teeth). In a healthy mouth, this scalloping effect is dictated by the cemento-enamel junction (CEJ) of the tooth which itself is also scalloped. It is this scalloping of the bony architecture which lends itself to the formation and maintenance of proper gingival contours including the inter-dental papilla (the small triangular flesh portion adjacent the gum line and located between the teeth).

However, despite best efforts of a person, or because of lack of proper dental care, it may become necessary to replace teeth completely. In these cases, dental implant procedures have proven to be an effective method of restoring both form and function in patients having missing teeth. Implants provide a structure upon which a prosthetic tooth or teeth can be attached and secured in an otherwise edentulous (non-tooth) area. In contrast to using dentures or other tooth born fixed or removable dental bridge systems, implants have the advantage of maintaining bone and not being subject to decay.

Bone support is necessary for proper placement, securement and maintenance of a dental implant. Proper bone support around an implant is also necessary for the development and maintenance of healthy gingival contours, including papilla. Bone growth around an implant follows the shape of the bone-integrating part of the implant. A primary concern in implant dentistry is the precise placement of an implant in its proper location, with appropriate and accurate angulation and rotational position at the time of implant placement surgery. Even the slightest error in implant placement can result in significant complications and or compromises in the stability of the implant, the maintenance of bone, the contours of the gingival tissues, placement of the final prosthesis, stability of the final prosthesis and the overall appearance of the patient's mouth.

Accordingly, it is desirable to provide a prefabricated dental implant surgical guide which ensures the proper placement of a dental implant or implants and its corresponding prosthesis (crown or crowns). One exemplary embodiment of the present invention allows it to be converted from a surgical guide to a dental provisional crown which can then be used to help maintain the hard (bone) and soft (gingival) tissue architecture of the mouth during the healing phase of treatment, with the end result being a final prosthesis that is stable, functional, natural looking and aesthetically pleasing in the patient's mouth.

For such applications, the prefabricated dental implant surgical guide of the present invention may be configured as a surgical guide with a tooth-shaped contour (also referred to as a "tooth contour") with a post affixed to its apical end, or with a post as an integral part of the entire guide. This embodiment of a dental implant surgical guide is placed into an initial osteotomy site (a surgical procedure in which bone is cut or prepared for the placement of a dental implant) at the time of dental implant placement surgery, but prior to final implant body placement, to ensure and or to correct proper location, angulation, and rotational position of an implant body prior to it's placement.

The present invention in various embodiments is a prefabricated dental implant placement surgical guide which, in one exemplary embodiment, has a post affixed to the apical end of an anatomically correct tooth form. This tooth form can be made to represent any tooth in the mouth in order to have accurate implant placement regarding the tooth to be replaced.

At the time of initial osteotomy site preparation, a small hole is prepared into the jaw bone using conventional dental implant surgical drills. The apical post of the surgical implant guide is inserted into the osteotomy site allowing verification of proper implant placement in location, angulation, and rotational position prior to implant body placement. This is accomplished by viewing the surgical guide in place, then comparing the tooth-contoured part of the surgical guide with some facial and/or intra-oral guideline such as the adjacent teeth, gingiva, shape of the arch and lips etc. This allows for proper implant location and ultimately placement to be verified or corrected prior to implant body placement lending to a more stable, functional and esthetic prosthetic outcome. The apical post of the surgical guide can repeatedly be inserted into the osteotomy site, as the site is further developed and deepened to continuously verify proper position and location of the implant body prior to its placement. This process of trying in the surgical guide with further osteotomy site preparation is repeated until the appropriate final depth of the osteotomy site is achieved. Thus the process of the present invention provides for a verified correct position, location and angulation of the osteotomy site, all prior to final implant body placement. If improper alignment is detected during this verification process, the osteotomy site location, angulation and position can be corrected with minimal damage to the bone.

In another embodiment of the present invention, the prefabricated dental implant surgical guide can be converted into a provisional crown, a plurality of crowns, or a bridge. This is accomplished by removing the finger grip and apical post, or guide post, hollowing out the tooth contour aspect of the guide, and relining the tooth contour aspect of the surgical guide, then reversibly fastening via screw or cement, the tooth contour aspect of the surgical guide to the abutment of an implant body.

In yet another embodiment, the surgical guide comprises a set of anatomically correct tooth forms each having an apical post and finger grip. The apical posts are graduated in length thus constituting a set of surgical guides that are sequentially used as an osteotomy site is created and deepened. In this way the surgical guide set can sequentially provide guidance that the osteotomy site is being correctly prepared.

In yet another exemplary embodiment, the prefabricated dental implant surgical guide comprises an anatomically correct tooth form having a bore through the tooth form into which an adjustable and removable post is placed or threaded. The apical end of the post protrudes through the tooth form and can be lengthened by pushing or screwing the post through the bore. In this way the apical end is lengthened and can be placed into the gradually deepening osteotomy site to insure that the site is correctly prepared. The post can also be removed and an osteotomy drill passed thru the bore to allow for further preparation of the osteotomy site with the guide in place. In another embodiment of the present invention, a bottom face of the apical end of the movable post comprises a marking agent. In this embodiment, the surgical guide is placed in a desired position on the jaw bone at a proposed osteotomy site. Once the correct position of the surgical guide is established, the movable post is pressed downward to engage the bottom face of the apical end with the jaw bone thereby marking the location of the osteotomy site.

In still another exemplary embodiment, the prefabricated dental implant surgical guide comprises a number of anatomically correct tooth forms as a unitary surgical guide. In this case, for example and without limitation, a number of tooth forms can be connected and tried into a series of side by side osteotomy sites as a unit. This allows multiple dental implants to be placed side by side with verification of proper location, angulation, and rotational position.

Thus various embodiments improve the dental implant placement process and allow for proper placement of a dental implant subsequent to osteotomy site preparation. Embodiments act as a prefabricated surgical guide and improve the placement of a dental implant. Embodiments further allow sequential placement of individual prefabricated implant surgical guides to develop sequential osteotomy sites for subsequent multiple side by side implant placement during dental implant placement surgery. Additional embodiments use unitary multi-tooth prefabricated implant surgical guides during dental implant placement surgery where more than one tooth is to be replaced with a dental implant. Other embodiments use a prefabricated dental implant surgical guide having adjustable apical posts for use with deepening osteotomy sites.

These and other embodiments will be come apparent to those skilled in the art upon review of the detailed description that follows.

DETAILED DESCRIPTION

Figure 1A:
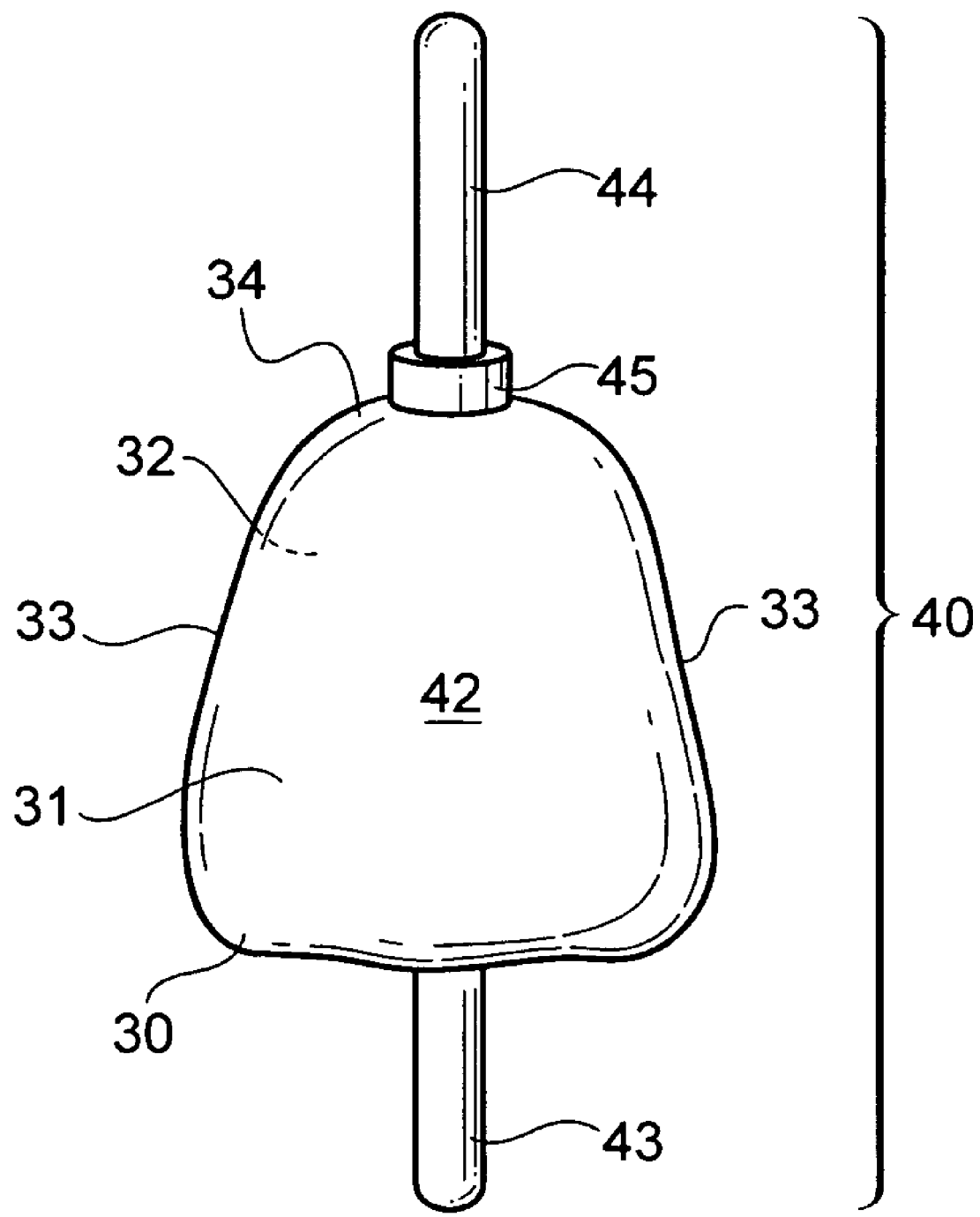
FIGS. 1a, 1b, and 1c illustrate a prefabricated dental implant surgical guide configured as a tooth with a static post.
Figure 1C:
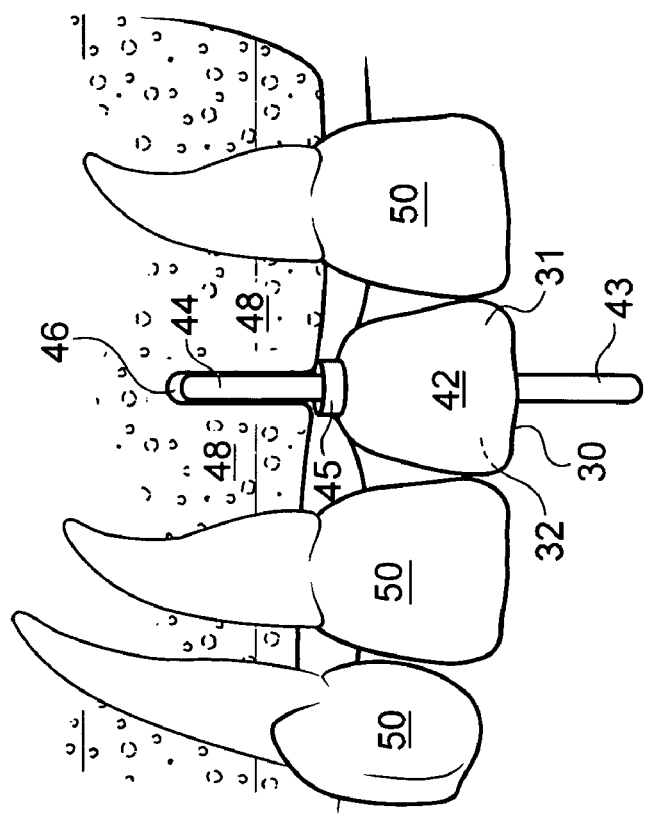
Figure 1B:
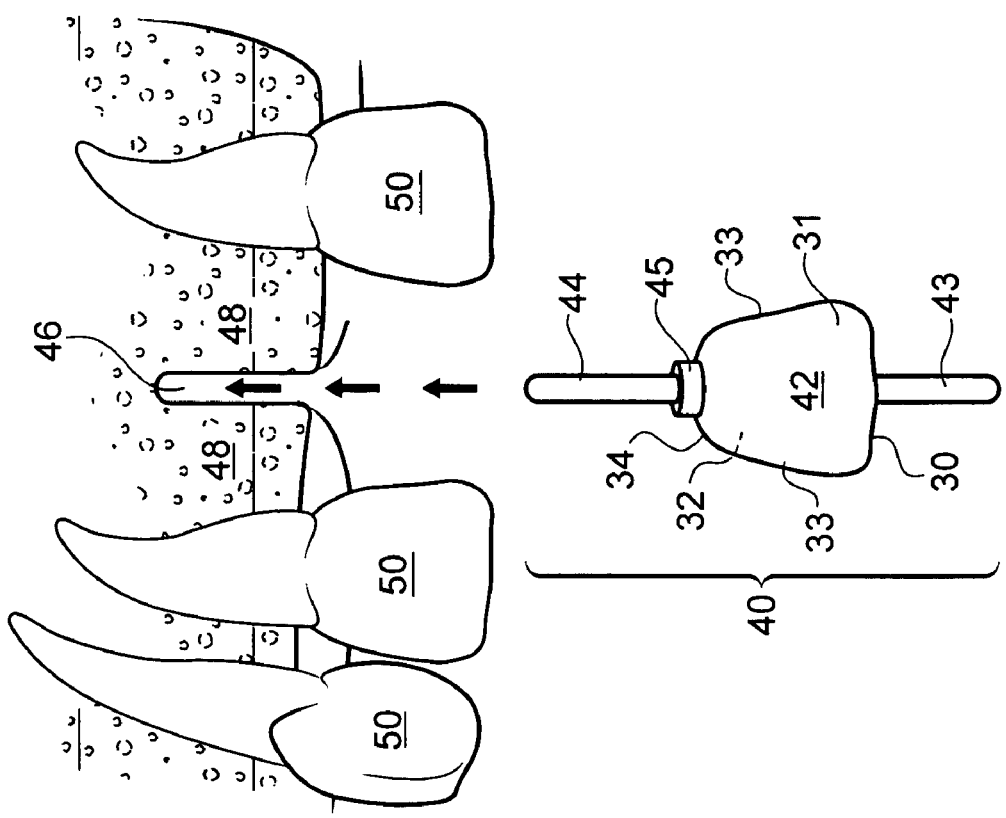

As noted above, the present invention comprises a method and apparatus for insuring correct placement of dental implants during the surgical placement process. Referring now to FIGS. 1a, 1b, and 1c, the prefabricated dental implant surgical guide configured as a surgical guide with a tooth-shaped contour with a post affixed to its apical end is illustrated. The guide can be made of metal, plastic, acrylic, porcelain or some other material known to those of skill in the dental arts. Such materials will be collectively referred to herein as "dental material." This exemplary embodiment is placed into an initial osteotomy site at the time of implant placement surgery, prior to implant body placement to ensure and or to correct the proper location, angulation, and rotational position of the implant body.

FIGS. 1a, 1b, and 1c illustrate the dental implant aid in an exemplary alternative embodiment. As illustrated in FIG. 1a, the dental implant aid, generally referred to as 40 in this figure, is configured as a one piece surgical guide with a tooth-shaped contour 42. The tooth-shaped contour 42 is further defined by its anatomical components, i.e. the incisal edge (for an anterior tooth) or occlusal table (for a posterior tooth) 30, facial contour 31, lingual contour 32, interproximal aspect 33 and apical aspect 34. Affixed to the apical end of tooth-shaped contour 42 is collar 45 which has apical post 44 extending above it. Affixed to the coronal end of tooth-shaped contour 42 is a protruding post which acts as finger grip 43. Thus the surgical guide 40 can be held in the mouth and the tooth-shaped contour 42 of guide 40 can be seen clearly by the surgeon during the course of surgery with out the surgeon's fingers obscuring the view.

This tooth-shaped contour 42 can be represented by any tooth shape found in the mouth (central incisors, lateral incisors, cuspids, premolars, and molars of both the upper and lower jaws) and can therefore be used as a surgical guide to verify implant body placement with respect to any tooth and its corresponding position in the mouth prior to implant placement. For example, FIG. 1b represents a jaw bone 48 to which an osteotomy site 46 (a surgical procedure in which bone is cut or prepared for the placement of an implant) has been prepared in jaw bone 48. As illustrated in FIGS. 1b and 1c, by holding finger grip 43, the apical post 44 of implant surgical guide 40 is placed into the osteotomy site 46 so that collar 45 of implant surgical 40 rests against jaw bone 48 at the opening of osteotomy site 46. This is done at the time of implant placement surgery, but prior to implant body placement.

By using existing intra-oral guidelines as a reference (i.e. adjacent teeth 50, lips, shape of the arch as but several examples), the tooth contour 42 and its corresponding anatomic components of implant surgical guide 40 with apical post 44 in osteotomy site 46, can be used to verify and/or correct the proper location, angulation, and rotational position of any implant body and it's corresponding system prior to it's insertion. This is accomplished by comparing the location, angulation, and position of the tooth shape-contour 42 and its corresponding anatomic components of the implant surgical guide 40 with some facial and/or intra-oral guideline or reference such as the adjacent teeth, gingiva, shape of the arch and lips, face etc., while apical post 44 of implant surgical guide 40 is engaged in osteotomy site 46.

Verification of osteotomy site position, angulation, location, subsequent proper implant location and placement and proper prosthesis location, requires the tooth contour aspect 42 of implant surgical guide 40 be in proper alignment with the facial and or intra-oral guide lines or references previously noted. This alignment is verified by comparing the position of the anatomic components of tooth contour 42, for example, the incisal edge (for an anterior tooth) or occlusal table (for a posterior tooth) 30, facial contour 31, lingual contour 32, interproximal aspect 33 and apical aspect 34 of tooth contour 42 of the surgical guide 40 while engaged in the mouth with facial and or intra -oral references previously noted.

If the alignment of the anatomic components of tooth contour 42 of surgical guide 40 are in harmony with and are symmetrical to the facial and or intra-oral references previously noted, osteotomy site location, position and angulation are verified, and osteotomy site and subsequent implant placement can be completed.

If there is disharmony and/or an asymmetrical position of the anatomic components of tooth contour 42 of the implant surgical guide 40 is noted with respect to the facial and or intra-oral references previously noted, a correction as to position and location can be made and verified prior to final implant placement.

It will be apparent to those skilled in the art that, not only can different tooth shapes be represented, but also different sizes of tooth contour 42 of the prefabricated dental implant surgical guide 40 can be used to conform to the size teeth and arch form of the dental implant patient.

Figure 2A:
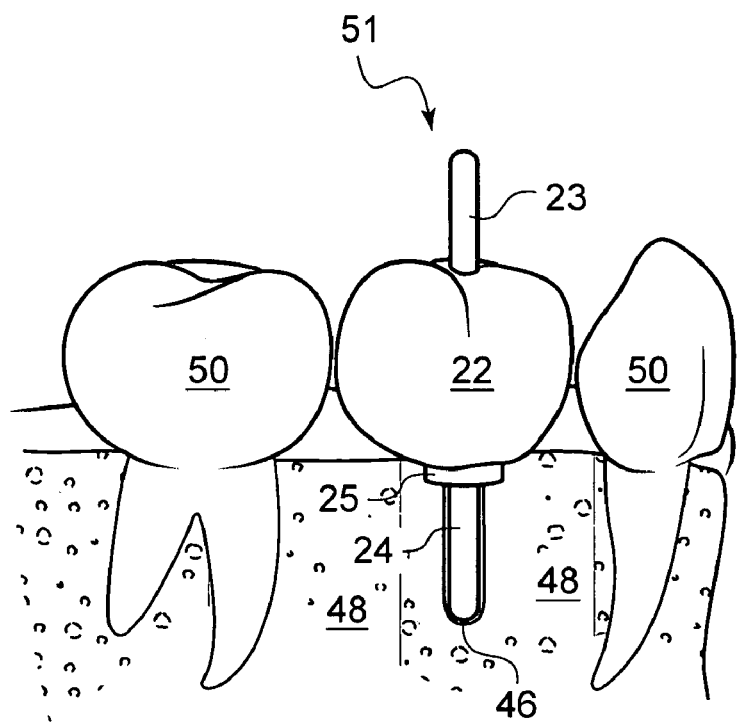
FIGS. 2a and 2b illustrate another embodiment of a prefabricated dental implant surgical guide converted to and also used as an interim crown with posts that are removable.
Figure 2B:
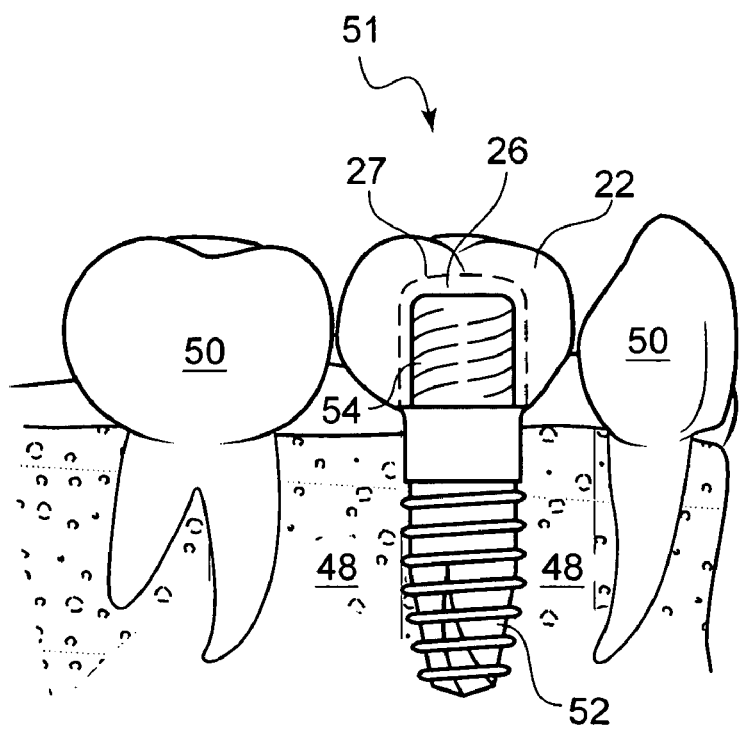

Referring now to FIGS. 2a and 2b, another alternate embodiment generally referred to as 51 is illustrated. In this embodiment, the prefabricated implant surgical guide is made of a dental material so that once implant placement has been verified and the implant body has been placed, either at the time of surgery or at a later date subsequent to healing, the surgical guide can be converted to a provisional crown as illustrated in FIGS. 2a and 2b.

Referring again to FIG. 2a, apical post 24 of implant guide 51 having a collar 25 is placed into osteotomy site 46 of jaw bone 48 to verify proper implant location and angulation prior to implant body placement as previously described in FIGS. 1a-c.

Referring now to FIG. 2b, implant body 52 is shown having been placed into jaw bone 48. At the time of surgery or subsequent to surgical healing, the finger grip 23 and apical post 24 of implant surgical guide 51 are removed via a cutting procedure known in the art. The tooth contour 22 of implant surgical guide 51 is then hollowed out so that a concavity 26 is formed on the internal aspect 27 of tooth contour 22 of implant guide 51. At the time of surgery or subsequent to surgical healing utilizing either a 2-stage, 2-piece implant system, a one-stage, 2-piece implant system or a one piece, one-stage implant system, the concavity 26 of internal aspect 27 of tooth contour 22 of implant guide 51 is relined with a dental provisional material, known to those in the art (for example and without limitation, acrylic) to the abutment aspect 54 of implant body 52 to create a custom fitting, retentive provisional crown which can then be either cemented into place with some provisional dental cement (for example and without limitation zinc oxide-eugenol)) or screw retained.

Referring now to FIGS. 3a, 3b, 3c and 3d, another embodiment of the prefabricated implant surgical guide, herein referred to as 53 having separate graduated apical post lengths is illustrated. In this embodiment, implant guide 53 exists in a multiple set format with apical posts 13, 15, and 17, connected to tooth contours 12, 14, and 16 respectively via collars 7, 9, and 11 respectively. Tooth contours 12, 14 and 16 are further defined by their anatomical components, that is, the incisal edge (for an anterior tooth) or occlusal table (for a posterior tooth) 1a, 1b and 1c respectively, facial contours 2a, 2b and 2c respectively, lingual contours 3a, 3b, and 3c respectively, interproximal aspects 4a, 4b and 4c respectively and apical aspects 5a, 5b and 5c respectively.

The tooth-shaped contours 12, 14 and 16 can be represented in the form of any tooth shape found in the mouth (central incisors, lateral incisors, cuspids, premolars, and molars of both the upper and lower jaws) and can therefore be used as a surgical guide to verify implant body placement with respect to any tooth and its corresponding position in the mouth prior to implant placement.

Apical posts 13, 15, and 17 increase in length to be used as described in FIGS. 3a, 3b, 3c and 3d. Finger grips 6, 8, and 10, respectively allow for manipulation of the surgical guide during the surgical implant placement procedure.

Figure 3A:
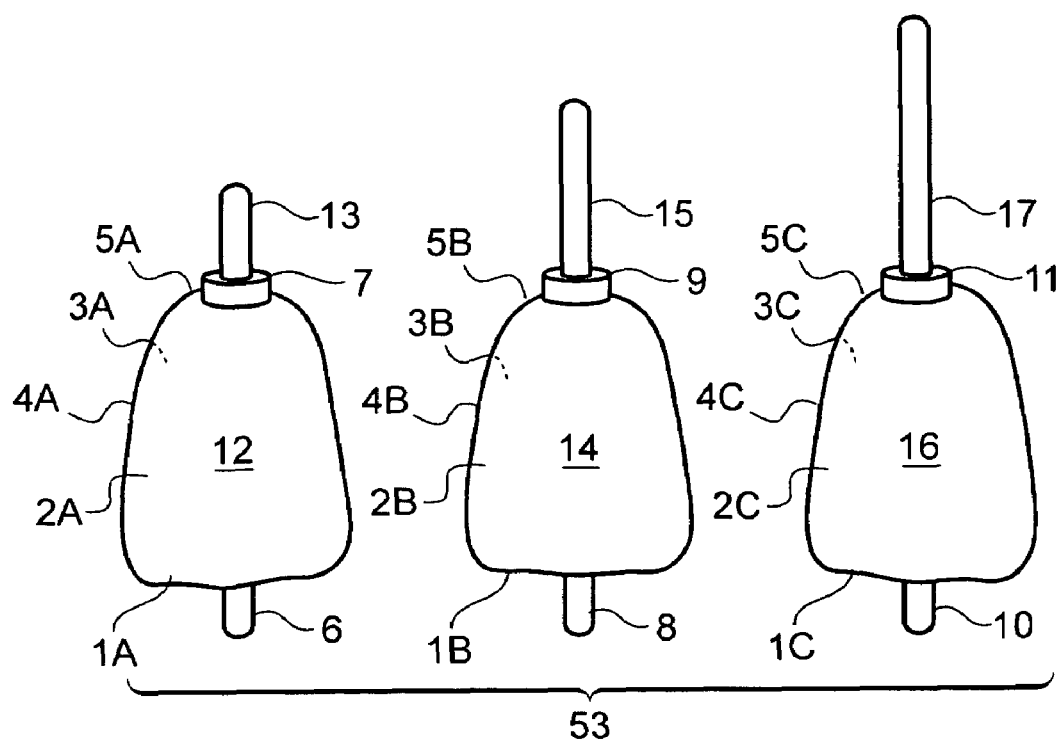
FIGS. 3a, 3b, 3c and 3d illustrate a prefabricated dental implant surgical guide as a series of tooth shapes having graduated post lengths.
Figure 3B:
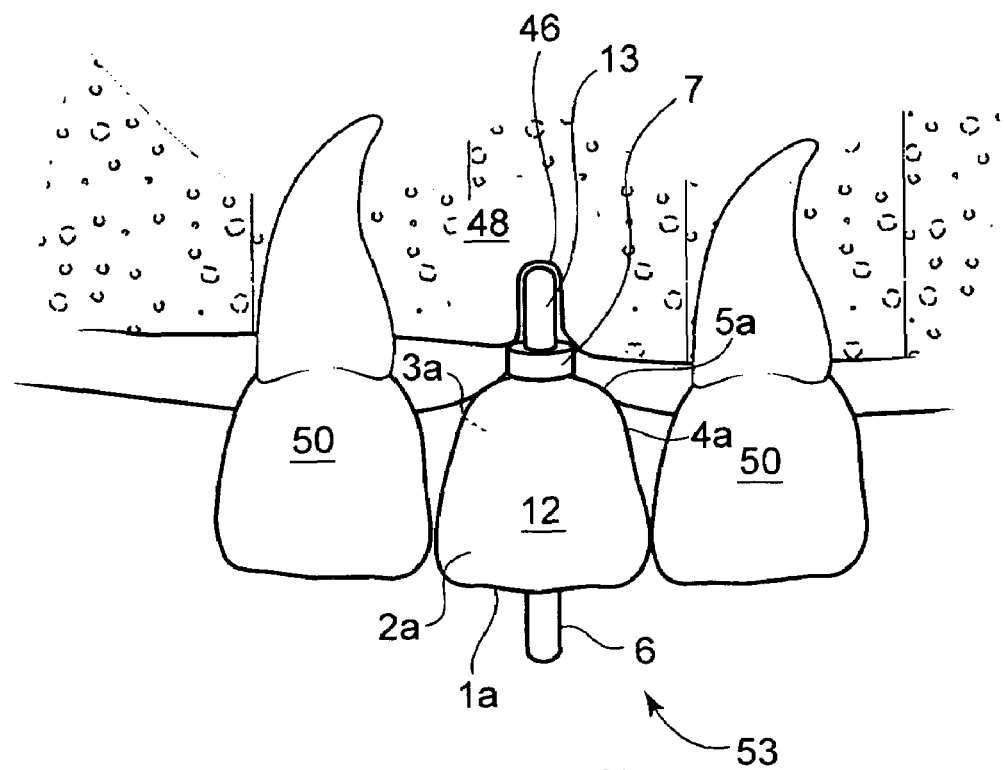

Referring now to FIG. 3b, the use of the embodiment of FIG. 3a is illustrated. An initial oseotomy site 46 of minimum depth is prepared into jaw bone 48. By placing implant guide 53 with the shortest apical post 13 first into initial osteotomy site 46, an initial and preliminary evaluation as to proper implant position, location and angulation can be done. At this time, verification and or correction to the initial osteotomy site 46 can be done with minimal trauma to jaw bone 48. This is accomplished by comparing the location, angulation and position of the tooth shape-contour 12 of the surgical guide 53 with some facial and/or intra-oral guideline or reference such as the adjacent teeth, gingiva, shape of the arch and lips, face etc. with apical post 13 of surgical guide 53 engaged in osteotomy site 46.

To verify osteotomy site position, angulation, location, subsequent proper implant location, angulation and placement and ultimately proper prosthesis location, requires the tooth contour aspect 12 of implant surgical guide 53 be in proper alignment with the facial and or intra-oral guide lines or references previously stated. This alignment is verified by comparing the anatomic components of tooth contour 12, that being the incisal edge or occlusal table 1a, facial contour 2a, lingual contour 3a, interproximal aspect 4a and apical aspect 5a of tooth contour 12 of surgical guide 53 while engaged in the mouth with facial and or intra-oral references previously noted.

If the alignment of the anatomic components of tooth contour aspect 12 of surgical guide 53 are in harmony with and are symmetrical to the facial and or intra-oral references previously noted, osteotomy site location, position and angulation are verified and osteotomy site and subsequent implant placement can be completed.

If there is disharmony and or an asymmetrical position of the anatomic components of tooth contour aspect 12 of implant surgical guide 53 is noted with respect to the facial and or intra-oral references previously noted, a correction as to position, angulation and location of the osteotomy site can be made and verified prior to final implant placement.

Figure 3C:
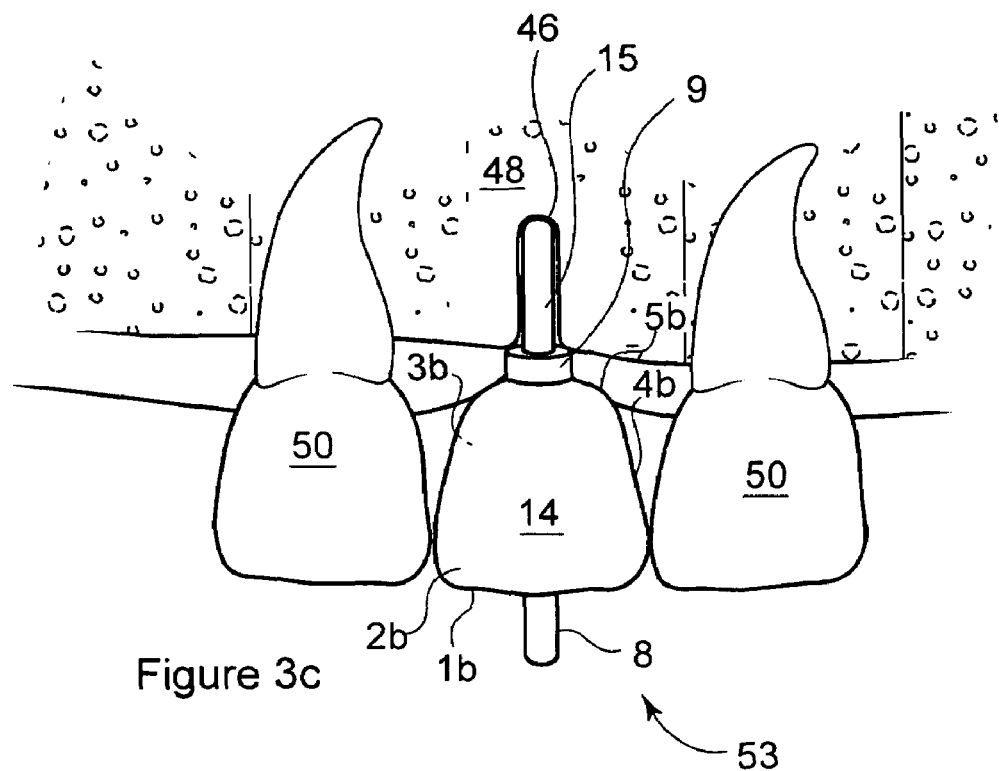
Figure 3D:
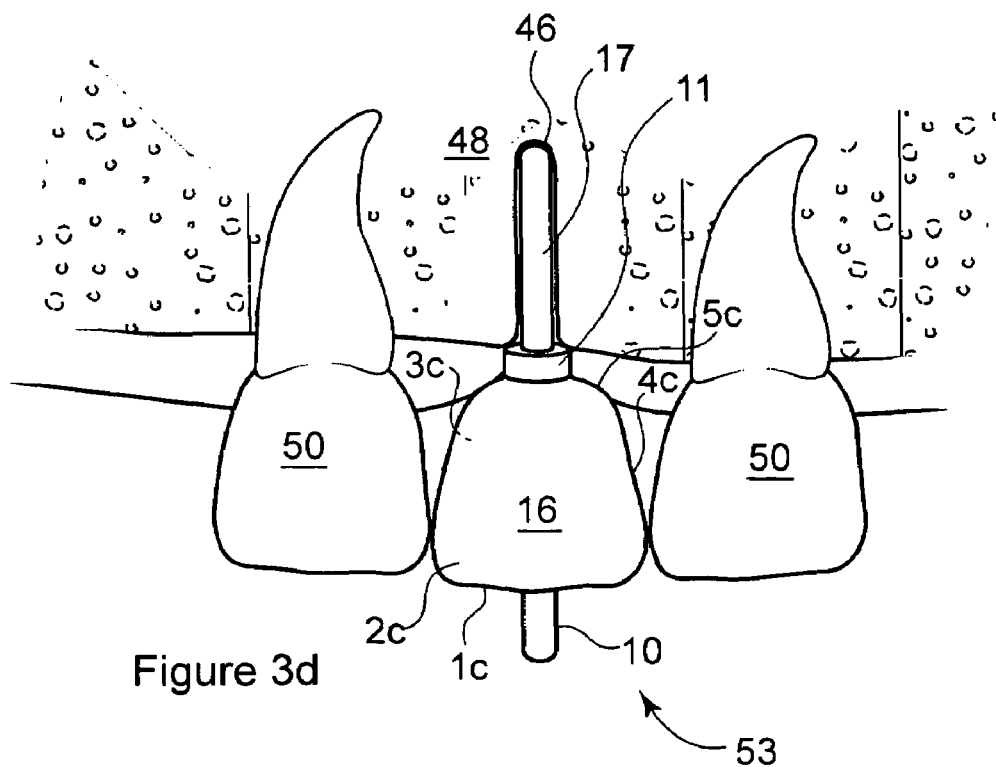

As illustrated in FIGS. 3c and 3d, as the osteotomy site 46 is deepened and developed, the implant guide 53 with the increasing apical post lengths 15 and 17 can be tried into deepening osteotomy site 46 to further verify and or to correct the position and or angulation of osteotomy site 46 prior to final implant body placement. This is accomplished by comparing the position of tooth contours 12, 14, and 16 (as the osteotomy site is deepened) of guide 53 with some other facial or intra-oral reference point (i.e. other teeth, gingiva, shape of the arch, lips, face, etc.) with posts 13, 15, and 17 of guide 53 sequentially engaged in osteotomy site 46. This verification process is accomplished as previously described in FIG. 3b. In this fashion, osteotomy site 46 is gradually prepared (deepened) and continuously verified during the preparation process to ensure accuracy in final location, angulation and position of the implant body and final prosthesis prior to its placement.

Referring now to FIGS. 4a, 4b, 4c and 4d, yet another embodiment of the prefabricated dental implant surgical guide generally referred to as 70 is illustrated. Implant surgical guide 70 comprises a tooth contour 62, collar 65, finger grip 63 and apical post 64. The tooth shaped contour 62 is further defined by its anatomical components: the incisal edge (for an anterior tooth) or occlusal table (for a posterior tooth) 61, facial contour 58, lingual contour 66, interproximal aspect 69 and apical aspect 71.

The tooth-shaped contour 62 can be represented by any tooth shape found in the mouth (central incisors, lateral incisors, cuspids, premolars, and molars of both the upper and lower jaws) and can therefore be used as a surgical guide to verify implant body placement with respect to any tooth and its corresponding position in the mouth prior to implant placement.

In this embodiment, the surgical guide 70 has a central bore 60 which extends the entire length of guide 70 (through tooth contour 62 and collar 65). This central bore 60 can be either smooth or threaded. An adjustable and removable post generally referred to as 67, comprises a central portion 68 which is located in central bore 60, finger grip portion 63 that extends beyond the coronal end of guide 70 and apical post portion 64 that extends beyond the apical end of guide 70. The central post portion 68 of post 67 remains in the central bore 60. Central post portion 68 and central bore 60 can be either smooth or threaded. If smooth, central post portion 68 of post 67 may be pushed through the central bore 60 thereby adjusting the length of apical post 64. If threaded, central post portion 68 of post 67 may be turned through central bore 60 thereby adjusting the length of apical post 64. In this fashion apical post portion 64 of adjustable removable post 67 can be adjusted and made shorter or longer to fit into a developing osteotomy site 46 to verify or correct final implant body location, position and angulation in jaw bone 48 prior to implant body placement.

During this process, as in other embodiments described above, proper implant location and position can be verified by comparing the position of tooth contour 62 of guide 70 with some other facial or intra-oral reference point (i.e. other teeth, gingiva, shape of the arch, lips, face, etc.) with apical post 64 of guide 70 engaged in osteotomy site 46.

Figure 4A:
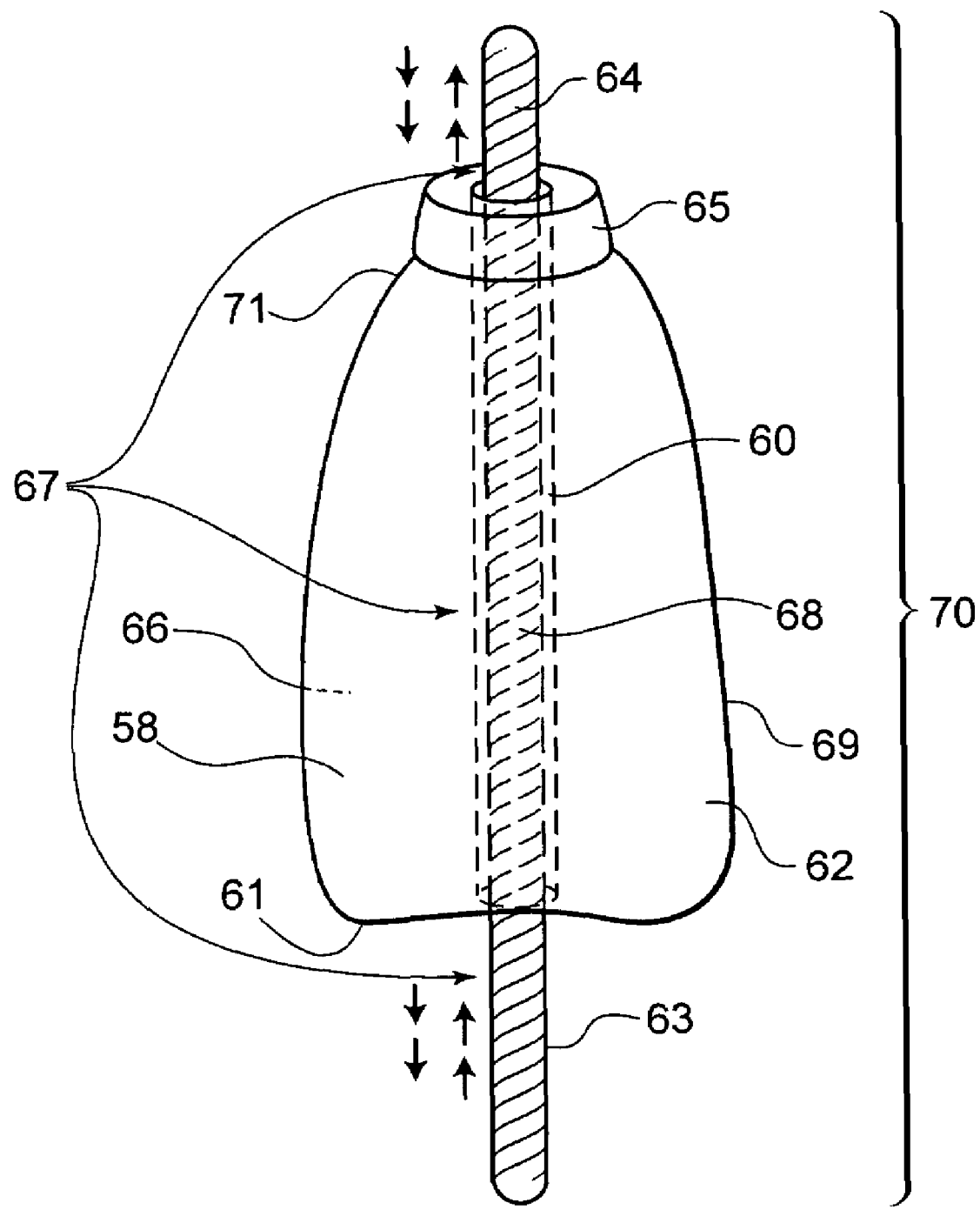
FIGS. 4a, 4b and 4c and 4d illustrate another embodiment as a prefabricated dental implant surgical guide having a central bore with an adjustable, removable post.
Figure 4B:
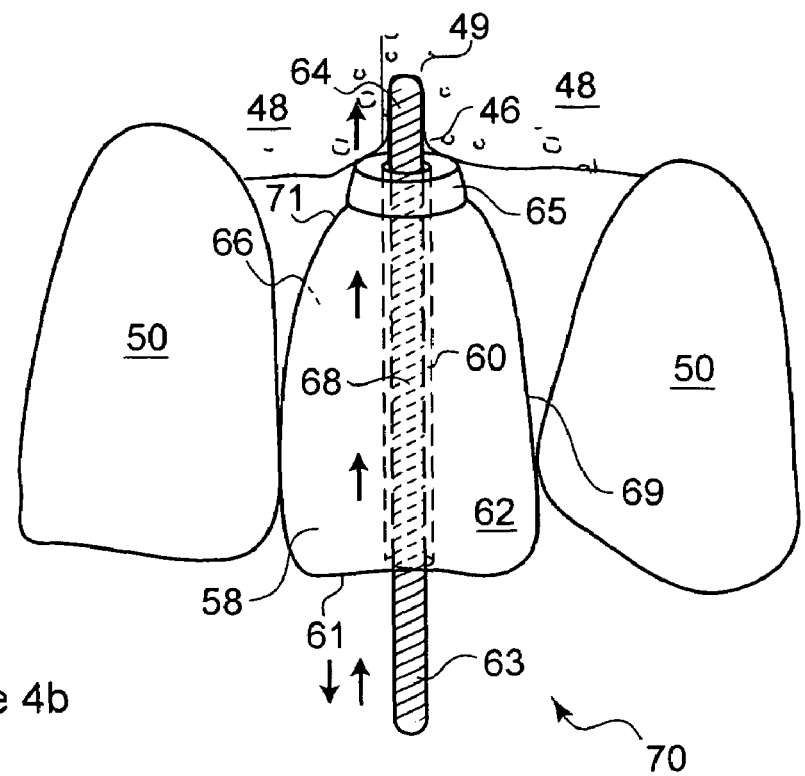

Referring now to FIG. 4b, an osteotomy site is identified, and an initial osteotomy site 46 of minimum depth is prepared in jaw bone 48. Surgical guide 70 is placed over osteotomy site 46. Finger grip portion 63 of adjustable, removable post 67 is pushed or turned so that central post portion 68 of adjustable, removable post 67 moves through central bore 60 increasing the length of apical post portion 64 of adjustable, removable post 67 until it engages the base 49 of osteotomy site 46. By comparing the position of tooth contour 62 of guide 70 with some other facial or intra-oral reference point (i.e. other teeth 50, gingiva, shape of the arch, lips, face, etc.), with apical post portion 64 of adjustable, removable post 67 of guide 70 engaged in osteotomy site 46, an initial verification or correction of position and or angulation of osteotomy site 46 can be done with minimal trauma to jaw bone 48.

This is accomplished by comparing the location, angulation and position of the tooth shape-contour 62 of the surgical guide 70 with some facial and/or intra-oral guidelines or references such as the adjacent teeth, gingiva, shape of the arch and lips etc. with apical post 64 of surgical guide 70 engaged in osteotomy site 46.

To verify osteotomy site position, angulation, location, subsequent proper implant location, angulation and placement and ultimately proper prosthesis location, requires tooth contour 62 of prefabricated dental implant surgical guide 70 be in proper alignment with the facial and or intra-oral guide lines or references previously stated. This alignment is verified by comparing the anatomic components of tooth contour 62, that being the incisal edge or occlusal table 61, facial contour 58, lingual contour 66, interproximal aspect 69 and apical aspect 71 of tooth contour 62 of surgical guide 70 while engaged in the mouth, with facial and or intra-oral references previously stated.

If the alignment of the anatomic components of tooth contour aspect 62 of surgical guide 70 are in harmony with and are symmetrical to the facial and or intra-oral references previously noted, osteotomy site location, position and angulation are verified and osteotomy site and subsequent implant placement can be completed.

If there is disharmony and or an asymmetrical position of the anatomic components of tooth contour 62 of implant surgical guide 70 is noted with respect to the facial and or intra-oral references previously noted, a correction as to position and location can be made and verified prior to final implant placement.

Figure 4C:
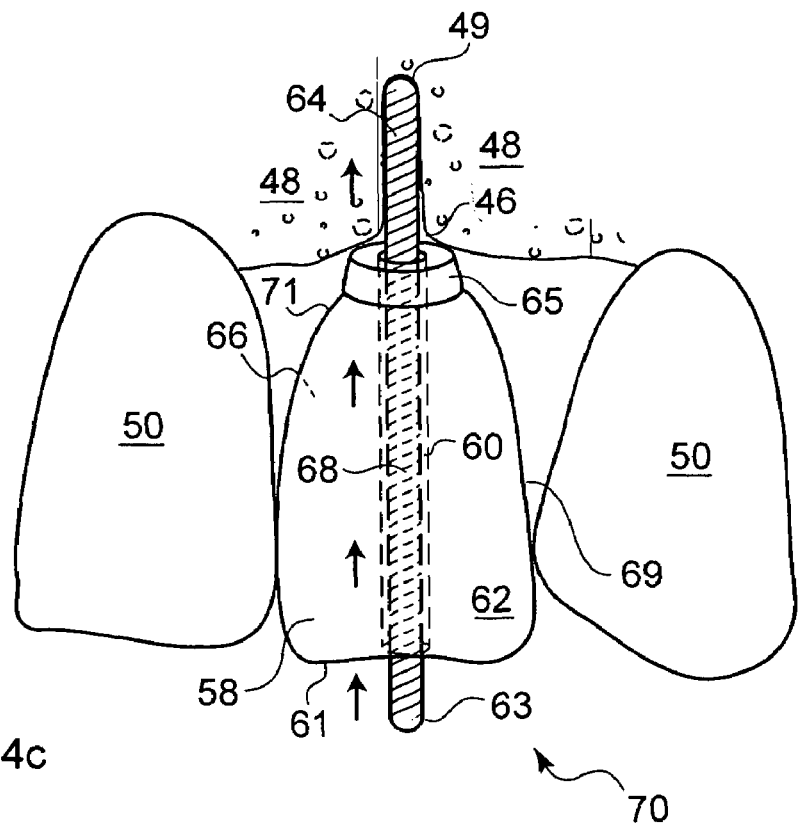

Referring now to FIG. 4c, as osteotomy site 46 is further deepened, guide 70 can repeatedly be placed over osteotomy site 46, with apical post portion 64 of adjustable, removable post 67 further lengthened into osteotomy site 46 by turning or pushing finger grip portion 63 of adjustable, removable post 67 (See FIG. 4a) to move central post portion 68 of adjustable, removable post 67 thru central bore 60, thus providing a means of continuous verification and or correction of position and or angulation of osteotomy site 46 prior to final implant body placement. Again, this is accomplished by comparing the position of tooth contour 62 of guide 70 with some other facial and or intra-oral reference point (i.e. other teeth 50, gingiva, shape of the arch, lips, face, etc.) with apical post portion 64 of adjustable, removable post 67 of guide 70 engaged in osteotomy site 46. This verification process is accomplished as previously described in FIG. 4b.

Figure 4D:
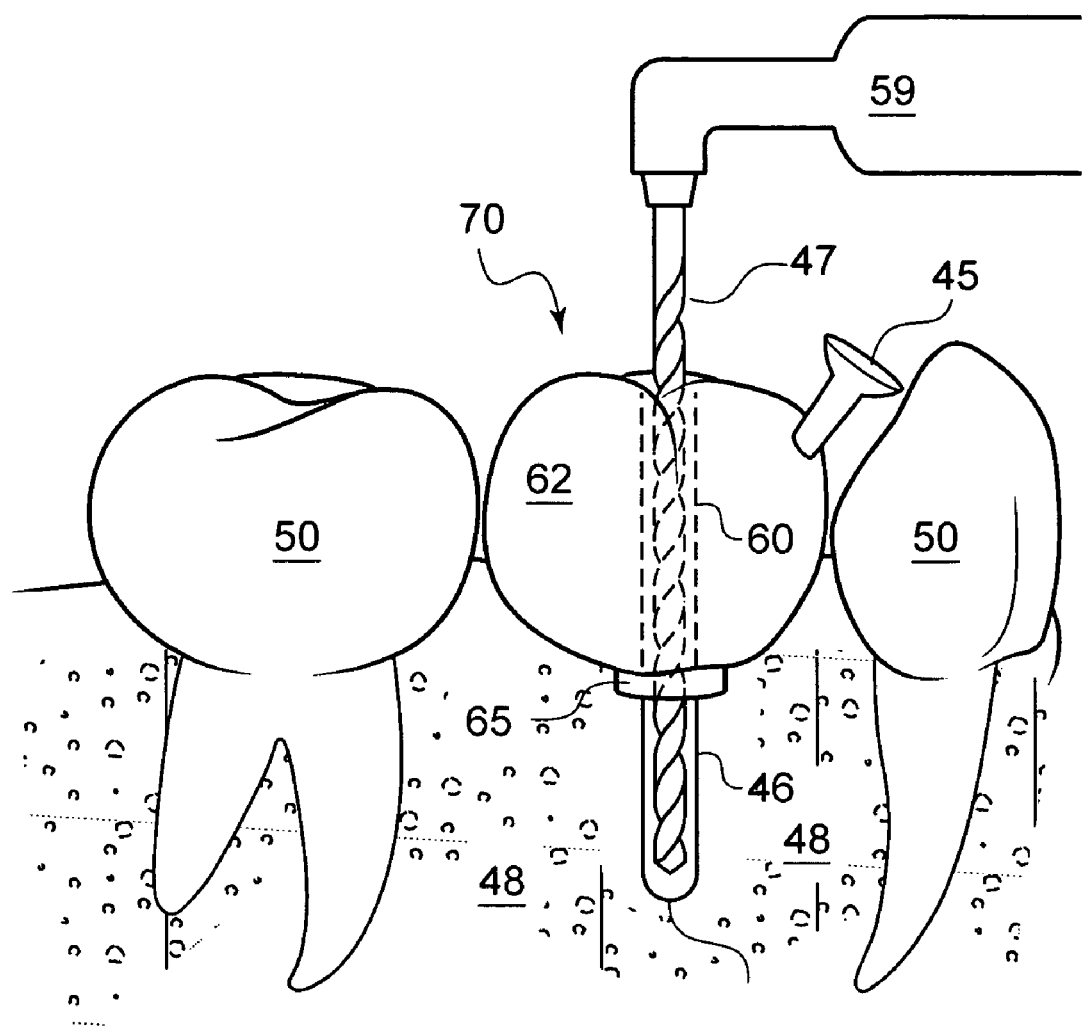

Referring now to FIG. 4d, adjustable, removable post 67 can be removed from surgical guide 70. Surgical guide 70 can be held in place in the mouth at osteotomy site 46 with a buccal and or lingual finger grip 45. By stabilizing guide 70 with buccal and or lingual finger grip 45, osteotomy bur 47 attached to surgical drill 59 can be placed thru central bore 60 of tooth contour 62 of implant guide 70 and activated allowing further preparation and continuous verification of osteotomy site 46 with surgical guide 70 in place in the mouth.

This verification process is accomplished as previously described in FIG. 4b.

As more fully explained below, in another embodiment, a bottom face of the apical end of the movable post comprises a marking agent. In this embodiment, the prefabricated dental implant surgical guide is placed in a desired position on the jaw bone at a proposed osteotomy site before a hole is drilled. Once the correct position and location of the osteotomy site is established, the movable post is pressed downward to engage the bottom face of the apical end with the jaw bone thereby marking the location of the osteotomy site.

Figure 5:
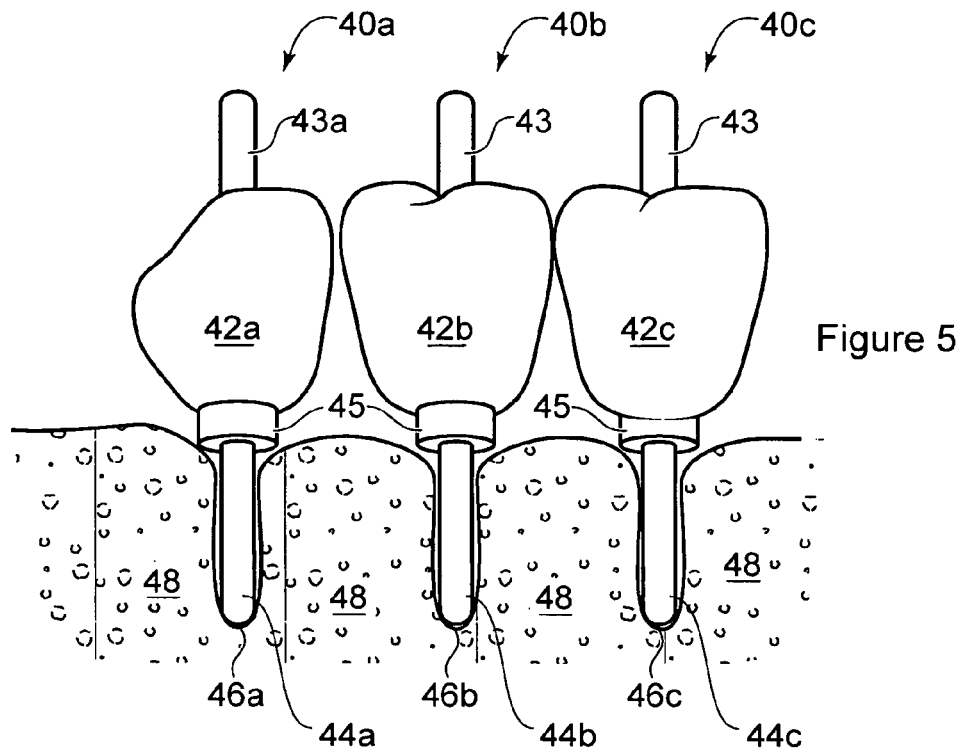
FIG. 5 illustrates an embodiment, as illustrated in FIGS. 1a-c, 2a-b, 3a-d and 4a-d being used in a multiple side by side format.

Referring now to FIG. 5, embodiments as illustrated in FIGS. 1-4 is described when placing multiple implants in a side by side format. Initial osteotomy sites 46a-c are identified, made and verified into jaw bone 48 as previously described. As an example, the most mesial osteotomy site 46a could be prepared and verified or corrected as previously described. Leaving the implant guide 40a in place, the next implant osteotomy site 46b can be prepared and verified or corrected as previously described. Now, leaving that implant guide 40b in place, another osteotomy site 46c can be prepared with implant guide 40c put in its place and verified or corrected as previously described. This type of verification process can be used to place implants side by side in a partially edentulous arch and or in a continuous fashion all the way around a completely edentulous arch. Thus all potential multi-unit side by side implant sites can be properly and accurately prepared, verified and or corrected prior to implant body placement.

Figure 6:
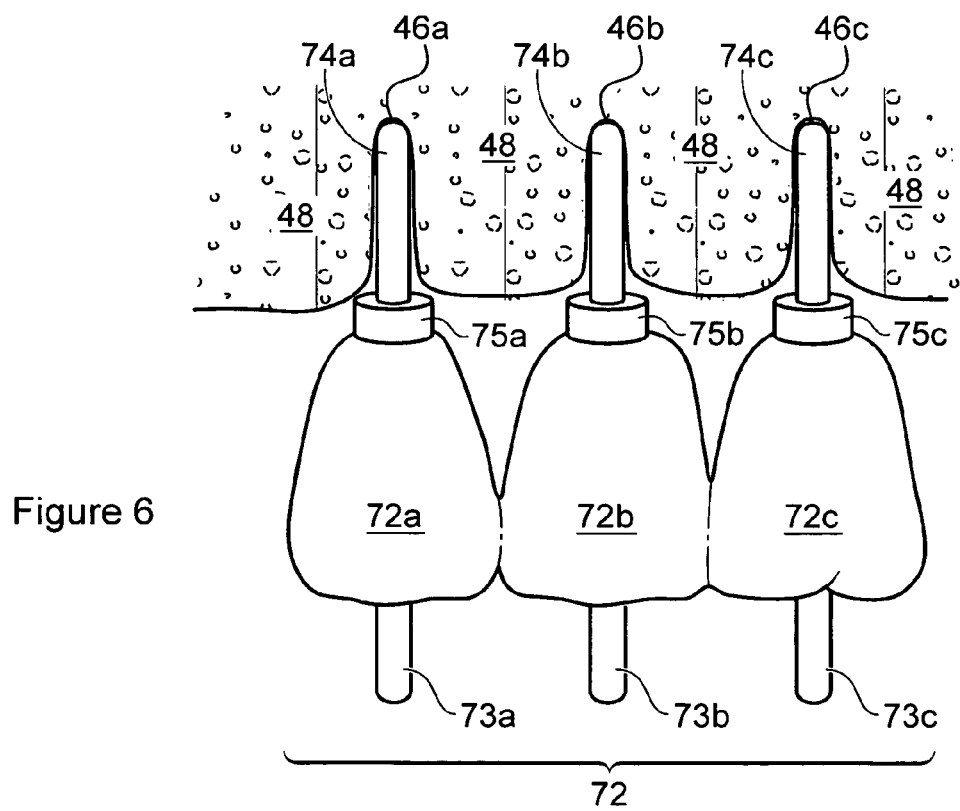
FIG. 6 illustrates another embodiment as a one piece multiple unit surgical guide.

FIG. 6 illustrates another embodiment of the present invention generally referred to as 72. In this embodiment, the surgical guide is formatted as a one piece, multi-unit surgical guide having tooth contours 72a, 72b, and 72c. Affixed to these tooth contours are collars 75a, 75b, and 75c, apical posts 74a, 74b, and 74c respectively, and corresponding finger grips 73a, 73b, and 73c respectively. The purpose of this embodiment is to guide the placement of multiple, side by side implants in a multi tooth edentulous site. Although formatted as such, guide 72 can be fabricated and used as described in FIGS. 1-4. In this embodiment, a proper guide size 72 and corresponding contour would be chosen that corresponds to the size and location of the edentulous site. Multiple initial osteotomy sites 46a-c would be made in jaw bone 48 with apical posts 74a, 74b, and 74c tried in osteotomy sites 46a-c to verify and or correct position, angulation and location of osteotomy sites 46a-c prior to implant body placement as previously described in FIGS. 1-4.

As will be appreciated by those skilled in the art, the multi-unit surgical guide may use movable (adjustable) posts as previously described in place of the fixed posts illustrated in FIG. 6.

Thus the embodiments as described may be used to guide the placement of dental implants in a single tooth format, multi tooth format and fully edentulous format.

Figure 7A:
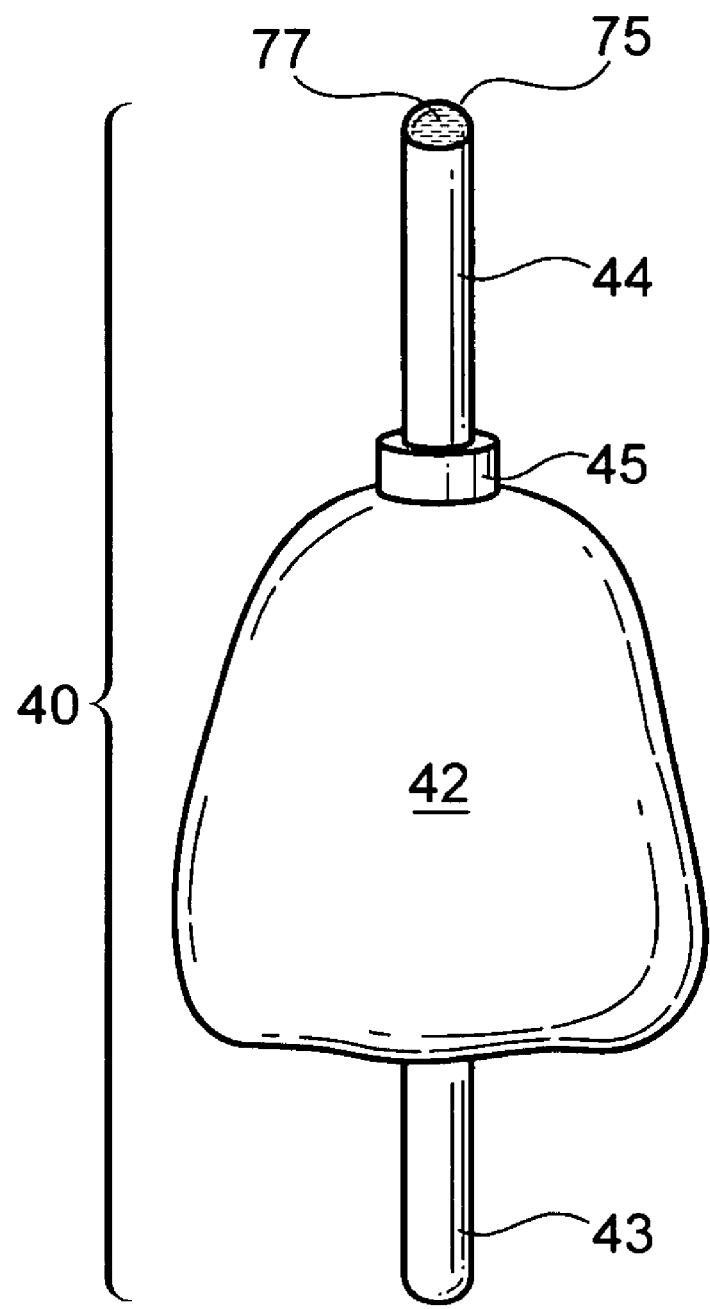
FIG. 7a-c illustrates an embodiment for the purpose of marking and identifying an osteotomy site.

Referring now to FIG. 7a, another embodiment of the prefabricated dental implant surgical guide 40 is illustrated. Surgical guide 40 as depicted in FIG. 1a, has fixed apical post 44 with bottom end face 75 and marking agent 77 on it for the purpose of marking and identifying an osteotomy site 46.

Figure 7C:
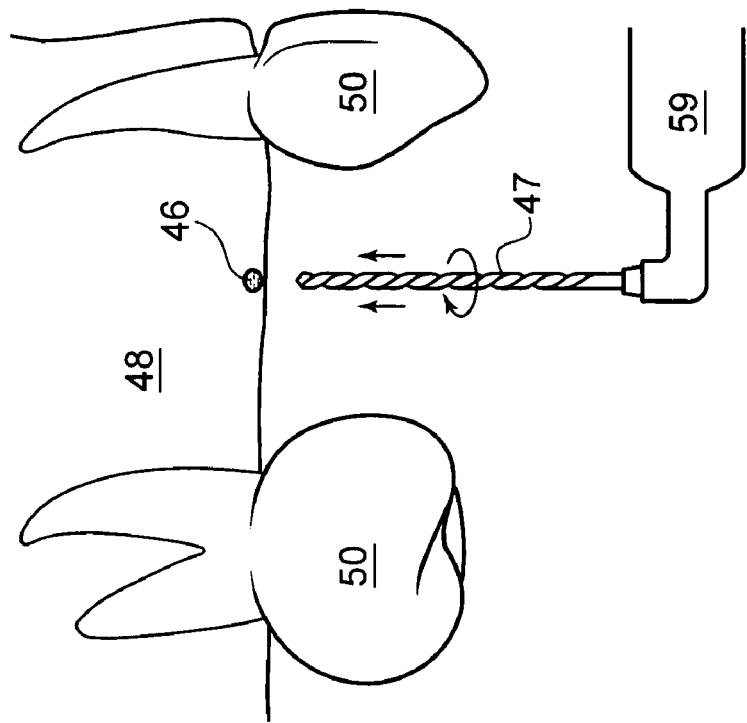
Figure 7B:
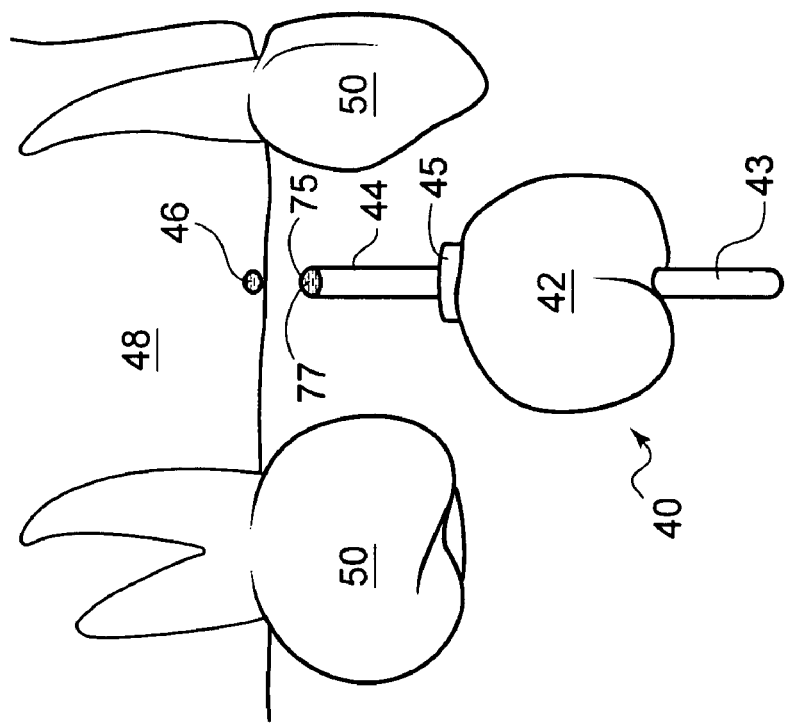

Referring now to FIGS. 7b and 7c use of the embodiment of FIG. 7a is illustrated. By holding coronal post 43 and by using tooth shaped contour 42 as a guide as previously described, osteotomy site 46 in jaw bone 48 can be located and demarcated by pressing end face 75 with marking agent 77 of fixed apical post 44 on top of jaw bone 48 leaving a mark denoting the osteotomy site 46. Osteotomy bur 47 of surgical drill 59 can then be used to initiate osteotomy site preparation. Further preparation, verification and completion of the osteotomy site 46 via drill 59 can then be accomplished as previously described in FIGS. 1b and 1c.

Figure 8A:
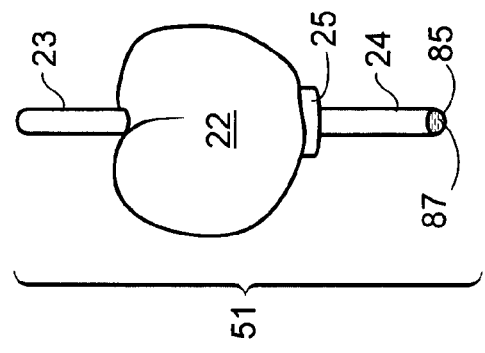
FIG. 8a-c illustrates another embodiment for the purpose of marking and identifying an osteotomy site.

Referring now to FIG. 8a, another embodiment of the prefabricated dental implant surgical guide 51 is illustrated. In this embodiment, surgical guide 51, comprises a fixed apical post 24 with bottom end face 85 and marking agent 87 on it for the purpose of marking and identifying an osteotomy site 46.

Figure 8C:
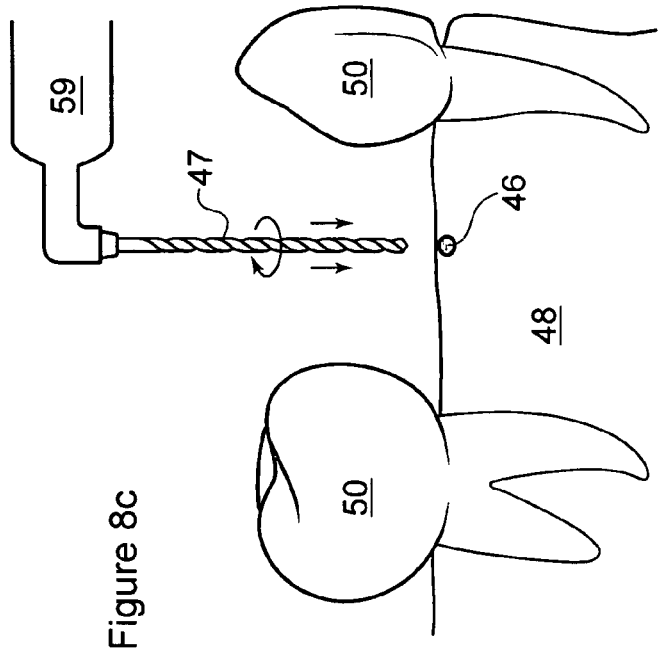
Figure 8B:
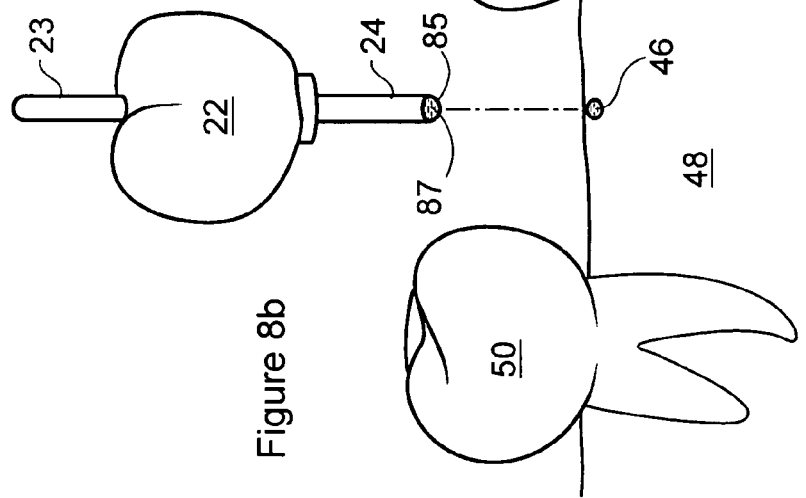

Referring now to FIG. 8b and 8c, by holding coronal post 23 and by using tooth shaped contour 22 as a guide as previously described, osteotomy site 46 in jaw bone 48 can be located and demarcated by pressing bottom end face 85 with marking agent 87 of fixed apical post 24 on top of jaw bone 48 leaving a mark denoting the osteotomy site 46. Osteotomy bur 47 of surgical drill 59 can then be used to initiate osteotomy site preparation. Subsequent to osteotomy site preparation and implant placement, the tooth shaped contour 22 of guide 51 can be converted to a provisional crown (immediate or delayed) as previously described in FIG. 2b.

Figure 9A:
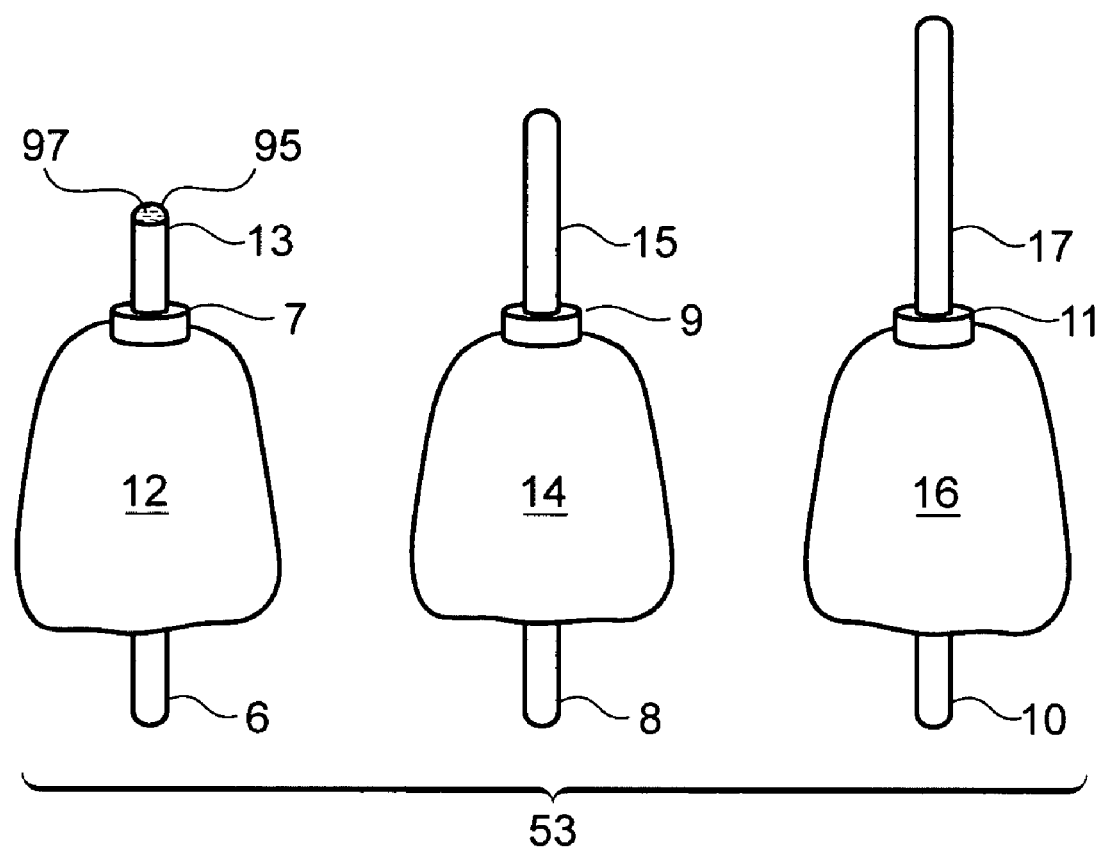
FIG. 9a-c illustrates another embodiment for the purpose of marking and identifying an osteotomy site.

Referring now to FIG. 9a, yet another embodiment of the prefabricated dental implant surgical guide 53 is illustrated. Surgical guide 53 comprises a fixed apical post 13 with bottom end face 95 and marking agent 97 on it for the purpose of marking and identifying an osteotomy site 46.

Figure 9C:
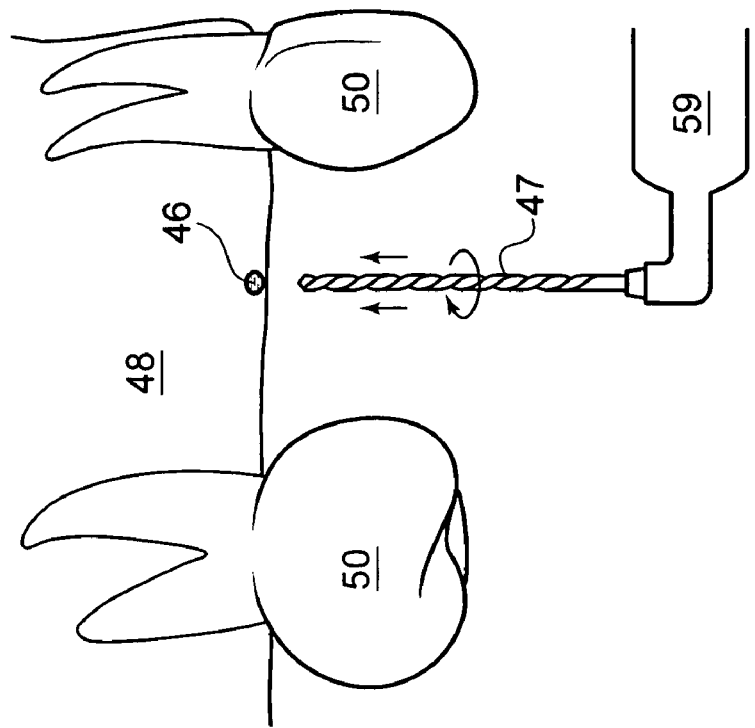
Figure 9B:
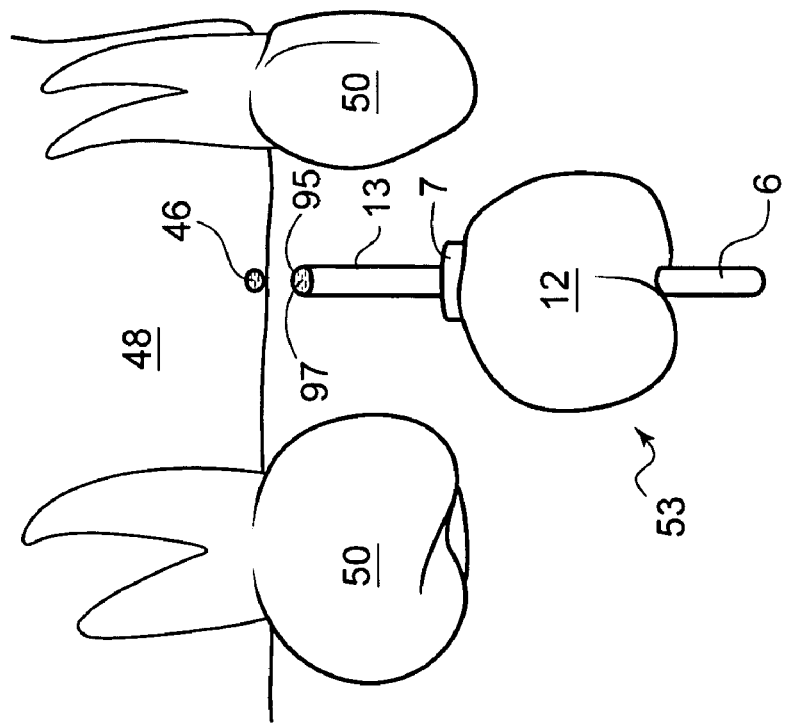

Referring now to FIGS. 9b and 9c, use of the surgical guide 53 is illustrated. By holding coronal post 6 and by using tooth shaped contour 12 as a guide as previously described, osteotomy site 46 in jaw bone 48 can be located and demarcated by pressing end face 95 with marking agent 97 of fixed apical post 13 on top of jaw bone 48 leaving a mark denoting the osteotomy site 46. Osteotomy bur 47 of surgical drill 59 can then be used to initiate osteotomy site preparation. Further preparation, verification and completion of the osteotomy site 46 can then be accomplished as previously described in FIGS. 3b, 3c and 3d.

Figure 10A:
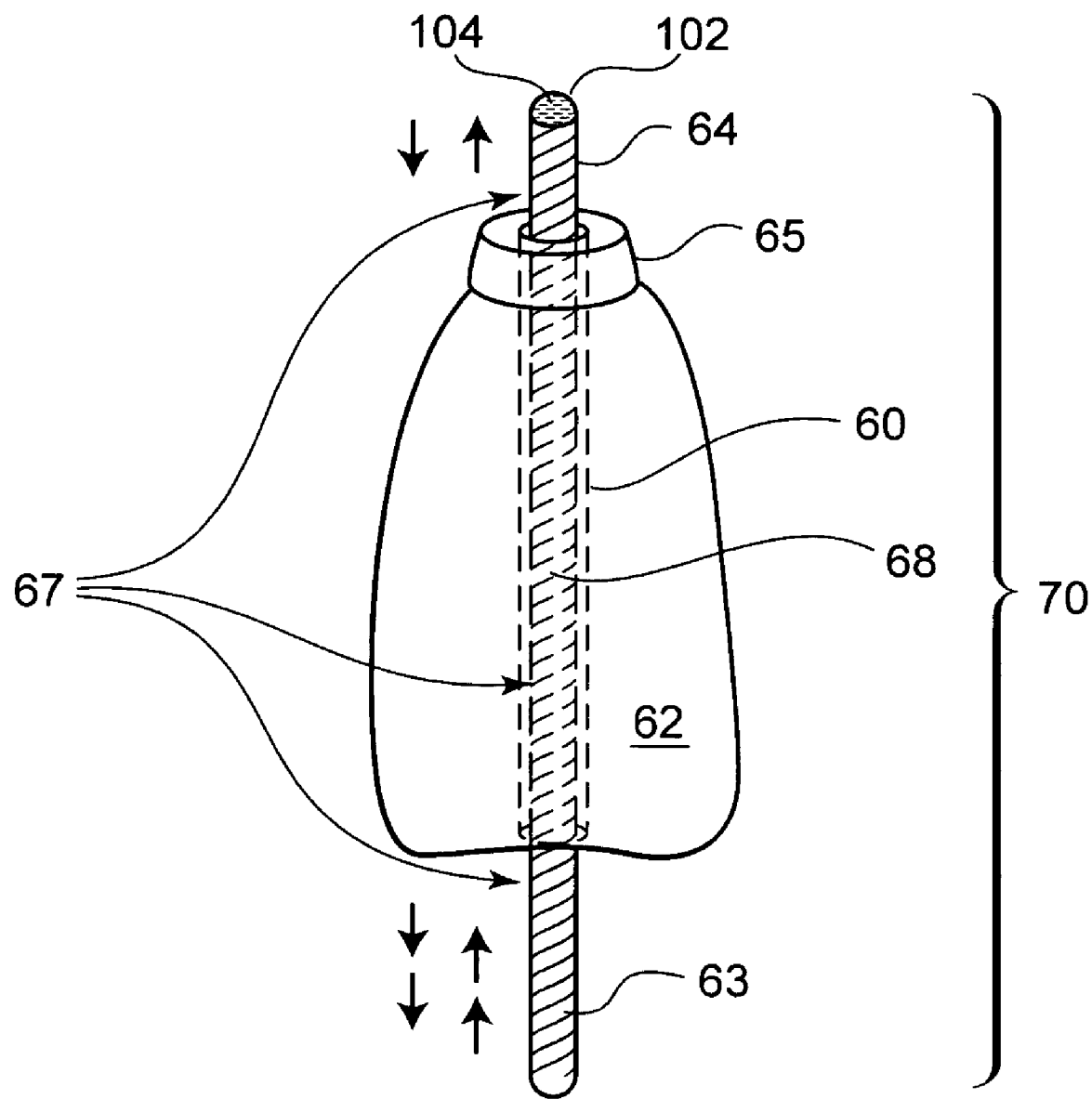
FIG. 10a-c illustrates another embodiment for the purpose of marking and identifying an osteotomy site.

Referring now to FIG. 10a, another embodiment of prefabricated dental implant surgical guide 70 is illustrated. Surgical guide 70 comprises an adjustable removable post 67 with apical post aspect 64 with a bottom end face 102, and marking agent 104 on it for the purpose of marking and identifying an osteotomy site 46.

Figure 10C:
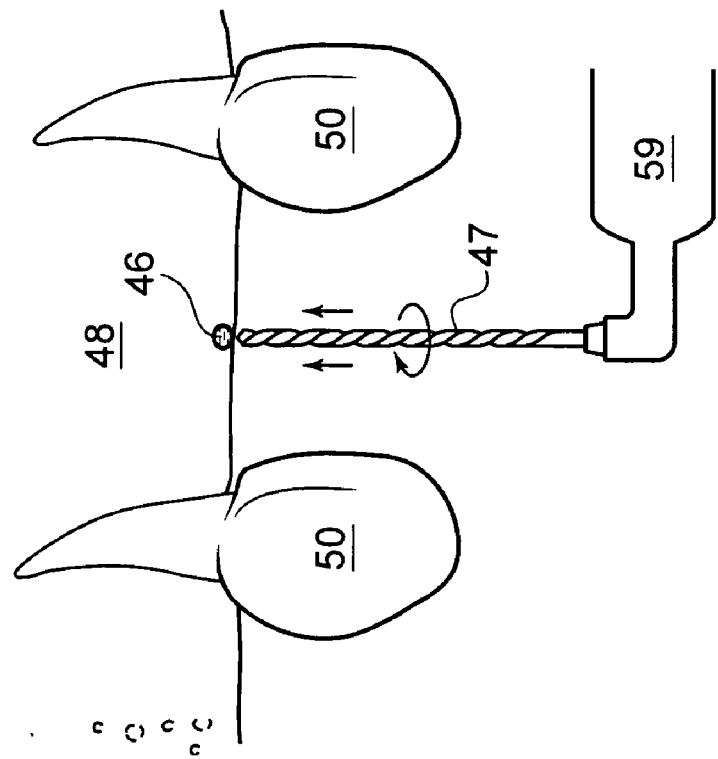
Figure 10B:
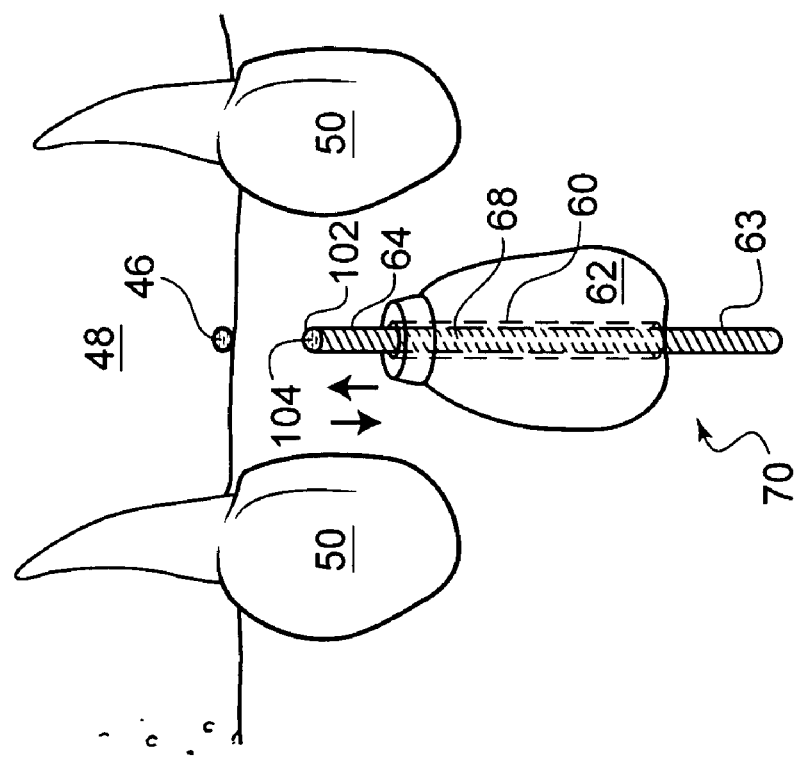

Referring to FIGS. 10b and 10c, use of the prefabricated dental implant surgical guide is illustrated. By pushing or turning coronal post 63 of adjustable removable post 67 so that central post portion 68 moves through central bore 60, thereby lengthening apical post portion 64 and by using tooth shaped contour 62 as a guide as previously described, osteotomy site 46 in jaw bone 48 can be located and demarcated by pressing end face 102 with marking agent 104 of apical post aspect 64 of adjustable removable post 67 on top of jaw bone 48 leaving a mark denoting the osteotomy site 46. Osteotomy bur 47 of surgical drill 59 can then be used to initiate osteotomy site preparation. Further preparation, verification and completion of the osteotomy site can then be accomplished as previously described in FIGS. 4b, 4c and 4d.

Figure 11A:
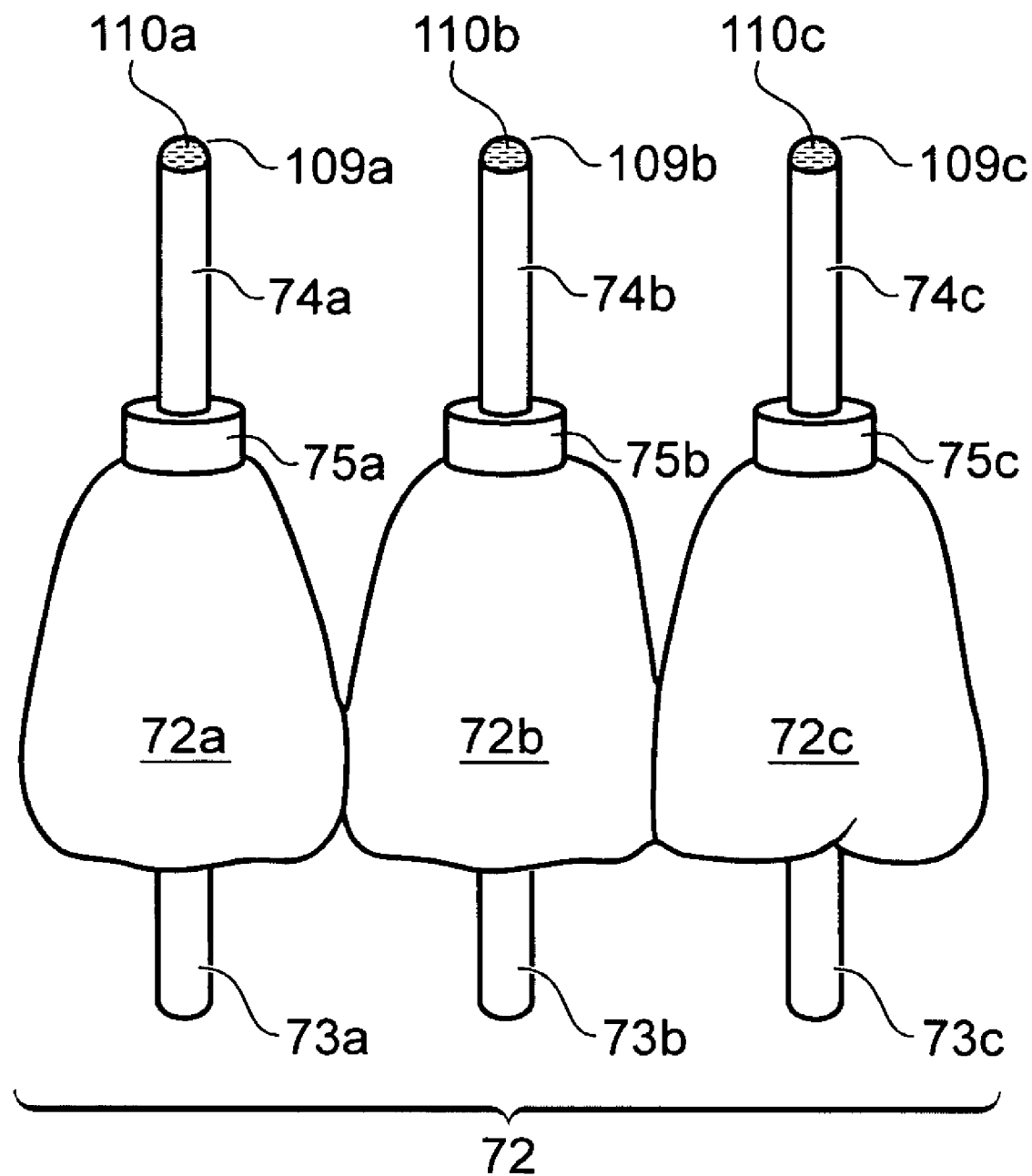
FIG. 11a-c illustrates another embodiment for the purpose of marking and identifying an osteotomy site.

Referring now to FIG. 11a, still another embodiment of prefabricated dental implant surgical guide 72 is illustrated. The multi unit one piece surgical guide 72 comprises fixed apical posts 74a, 74b, and 74c with bottom end faces 109a, 109b and 109c and with marking agents 110A, 110b, and 110c on them for the purpose of marking and identifying an osteotomy sites 46a, 46b and 46c.

Figure 11B:
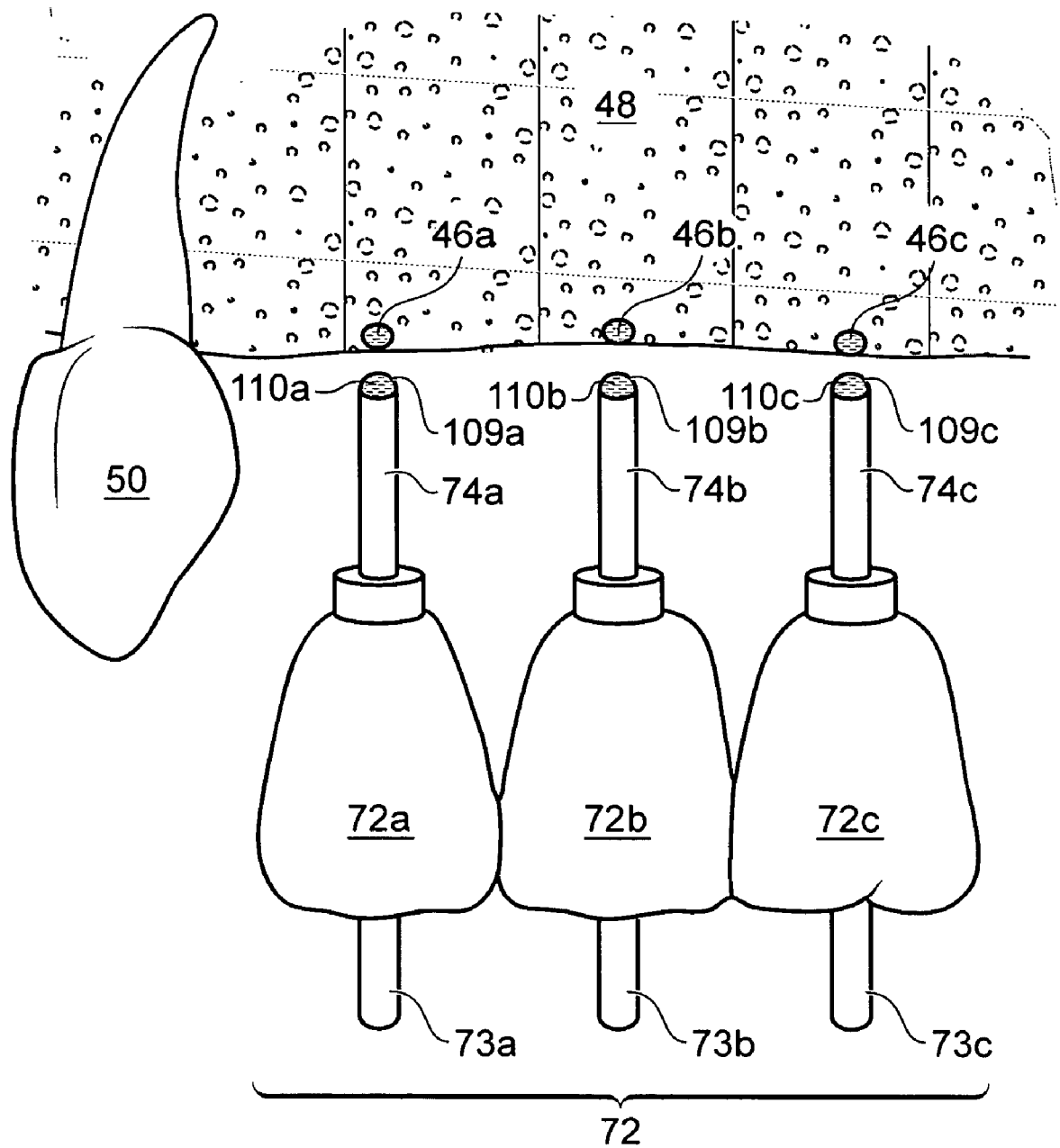
Figure 11C:
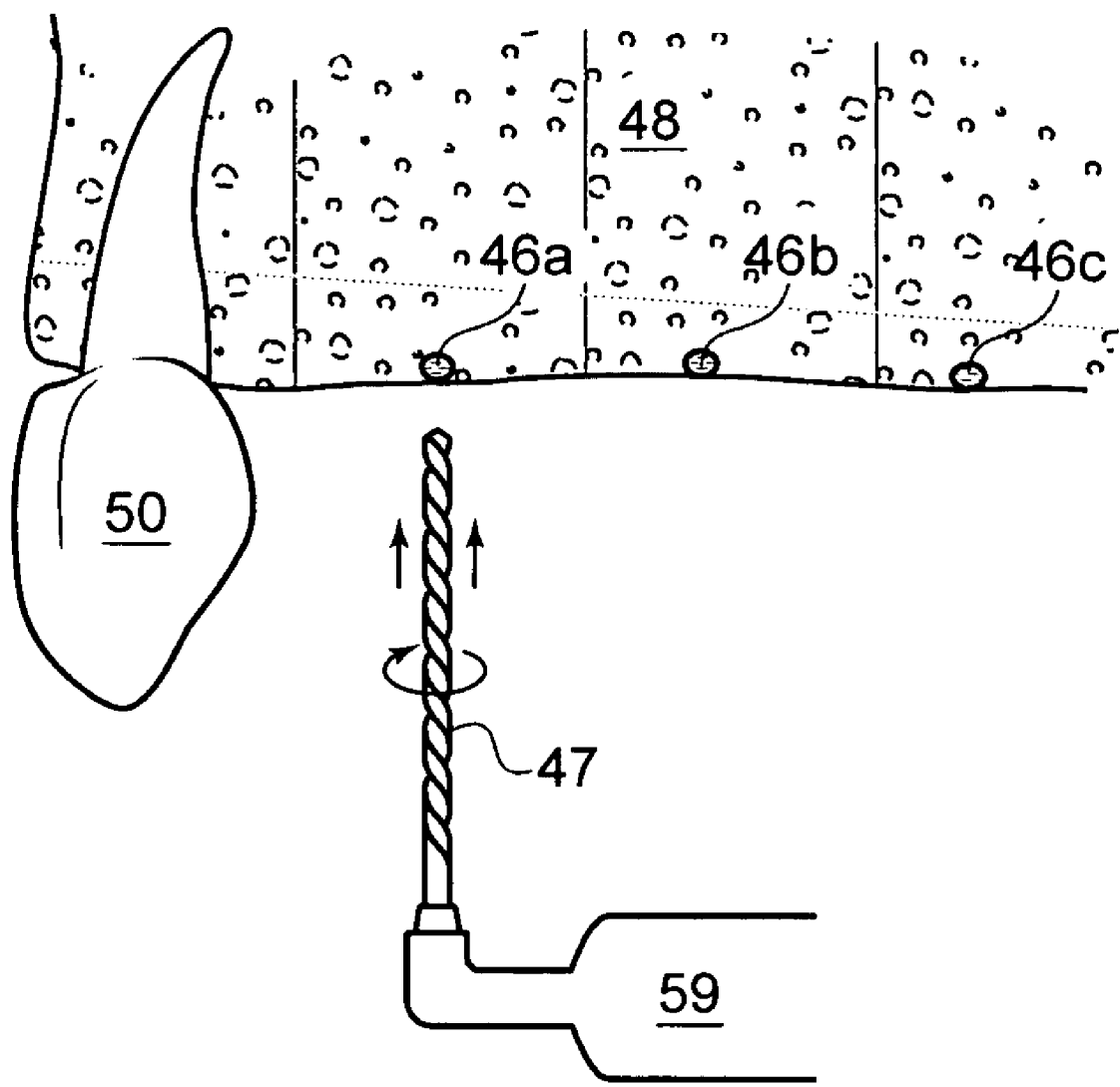

Referring now to FIGS. 11b and 11c, use of the prefabricated dental implant surgical guide is illustrated. By holding coronal posts 73a, 73b and or 73c and by using tooth shaped contour 72a, 72b and 72c as a guide as previously described, osteotomy sites 46a, 46b and 46c in jaw bone 48 can be located and demarcated by pressing end faces 109a, 109b and 109c with marking agents 110a, 110b and 110c of fixed apical posts 74a, 74b and 74c on top of jaw bone 48 leaving marks denoting the osteotomy sites 46a, 46b and 46c. Osteotomy bur 47 of surgical drill 59 can then be used to initiate osteotomy site preparations. Further preparation, verification and completion of the osteotomy sites can then be accomplished as previously described in FIGS. 1-4.

A method and apparatus for using a prefabricated implant surgical guide during dental implant placement surgery has now been illustrated. It will also be understood that the invention may be embodied in other specific forms without departing from the scope of the invention disclosed and that the examples and embodiments described herein are in all respects illustrative and not restrictive. Those skilled in the art of the present invention will recognize that other embodiments using the concepts described herein are also possible. Further, any reference to claim elements in the singular, for example, using the articles "a," "an," or "the" is not to be construed as limiting the element to the singular.

What is claimed is:

1. A method for dental implant surgery comprising:
   placing a prefabricated implant surgical guide in the mouth of a recipient at an implant site;
   the prefabricated implant surgical guide consisting essentially of a single tooth-shaped contour having an apical end and a coronal end; and
   a post affixed to the apical end of the tooth-shaped contour, the apical end post comprising a bottom face and a marking agent on the bottom face;
   marking an implant osteotomy site via the marking agent on the bottom face of the apical post;
   drilling a hole at the osteotomy site to an initial depth;
   placing the prefabricated implant surgical guide apical end post into the hole at the osteotomy site, wherein the apical end post is dimensioned to fit within the hole of the osteotomy site; and
   verifying the positional and angular alignment of the osteotomy site upon insertion of the apical end post into the hole of the osteotomy site.

2. The method for dental implant surgery of claim 1, wherein the apical end post comprises a length approximating a final depth of the osteotomy site.

3. The method for dental implant surgery of claim 1, wherein verifying the alignment of the osteotomy site comprises verifying the proper location, angulation, and rotational position of the tooth-shaped contour by comparing the tooth-shaped contour of the prefabricated dental implant surgical guide to other dental features of a patient with the apical end post of the surgical guide engaged in the osteotomy site.

4. The method for dental implant surgery of claim 1, wherein the tooth-shaped contour is selected from the group consisting of a central incisor shape, a lateral incisor shape, a cuspid shape, a premolar shape, and a molar shape of an upper and lower jaw.

5. The method for dental implant surgery of claim 1, further comprising placing the tooth-shaped contour apical end at a proposed osteotomy site, causing the bottom face of the apical post to contact a jaw bone at the proposed osteotomy site thereby marking a drill site at the osteotomy site with the marking agent.

6. A method for dental implant surgery using a prefabricated dental implant surgical guide consisting essentially of a single tooth-shaped contour having an apical end and associated bottom face and a coronal end, the tooth-shaped contour comprising a central bore along an axis extending from a center of an apical end through a center of a coronal end and an adjustable removable post located in the central bore, wherein the post comprises a post apical end that extends beyond the apical end of the tooth-shaped contour and a post coronal end that extends beyond the coronal end of the tooth-shaped contour, where in the method comprises:
   placing the tooth-shaped contour in the mouth of a recipient at an implant site;
   marking an implant osteotomy site via a marking agent on a bottom face of the apical end of the adjustable removable post;
   drilling a hole at an osteotomy site to an initial depth;
   placing the post apical end into the hole at the osteotomy site;
   adjusting the length of the post apical end to the initial depth of the hole at the osteotomy site by manipulating the coronal end thereby extending the post apical end to the initial depth of the hole at the osteotomy site; and
   verifying the alignment of the hole at the osteotomy site upon insertion of the apical end post into the hole at the osteotomy site by comparing the tooth-shaped contour position of the surgical guide to other dental features of a patient.

7. The method for dental implant surgery of claim 6, wherein placing the adjustable removable post apical end of the tooth-shaped contour into the hole at the osteotomy site comprises positioning the post apical end of the tooth-shaped contour into the hole at the site using the coronal end of the adjustable removable post to position the surgical guide.

8. The method for dental implant surgery of claim 6 further comprising deepening the osteotomy site hole to a final depth, and verifying the location, position and angulation of the osteotomy site by manipulating the coronal end of the adjustable removable post, thereby allowing the apical end to engage the depth of the osteotomy site; and
   comparing the tooth-shaped contour position to other dental features of a patient.

9. The method for dental implant surgery of claim 6 further comprising:
   removing the adjustable removable post from the central bore of the tooth-shaped contour; and
   placing an osteotomy drill through the central bore of the tooth-shaped contour while the tooth-shaped contour is engaged in the mouth of the recipient, thereby allowing the initial depth of the osteotomy site to be developed.

10. The method for dental implant surgery of claim 9 further comprising:
    removing the adjustable removable post from the central bore of the tooth-shaped contour; and
    placing an osteotomy drill through the central bore of the tooth-shaped contour while the tooth-shaped contour is engaged in the mouth of the recipient, thereby allowing a final depth of the osteotomy site to be developed.

11. The method for dental implant surgery of claim 6, wherein the shape of the tooth-shaped contour is selected from the group consisting of a central incisor shape, a lateral incisor shape, a cuspid shape, a premolar shape, and a molar shape of an upper and lower jaw.

12. The method for dental implant surgery of claim 1 further comprising:
    drilling the hole at the osteotomy site to a final depth;
    placing the prefabricated implant surgical guide apical end post into the hole at the osteotomy site, wherein the apical end post is dimensioned to fit within the hole of the osteotomy site; and
    verifying the positional and angular alignment of the osteotomy site upon insertion of the apical end post into the hole of the osteotomy site.

* * * * *